(12) United States Patent
Johansson et al.

(10) Patent No.: US 9,381,243 B2
(45) Date of Patent: Jul. 5, 2016

(54) METHODS OF IDENTIFYING CRITICALLY ILL PATIENTS AT INCREASED RISK OF DEVELOPMENT OF ORGAN FAILURE AND COMPOUNDS FOR THE TREATMENT HEREOF

(71) Applicant: Rigshospitalet, Copenhagen (DK)

(72) Inventors: Pär Johansson, Dösjebro (SE); Sisse Rye Ostrowski, Gentofte (DK)

(73) Assignee: Rigshospitalet, Kobenhavn Ø (DK)

( * ) Notice: Subject to any disclaimer, the term of this patent is extended or adjusted under 35 U.S.C. 154(b) by 3 days.

(21) Appl. No.: 14/329,350

(22) Filed: Jul. 11, 2014

(65) Prior Publication Data
US 2014/0322207 A1 Oct. 30, 2014

Related U.S. Application Data

(62) Division of application No. 13/142,935, filed as application No. PCT/DK2009/050357 on Dec. 30, 2009, now Pat. No. 8,877,710.

(60) Provisional application No. 61/161,487, filed on Mar. 19, 2009.

(30) Foreign Application Priority Data

Dec. 30, 2008 (DK) .................. 2008 01844

(51) Int. Cl.
| | | |
|---|---|---|
| A61K 38/36 | (2006.01) | |
| A61K 31/34 | (2006.01) | |
| A61K 39/395 | (2006.01) | |
| A61K 31/557 | (2006.01) | |
| A61K 31/727 | (2006.01) | |
| A61K 45/06 | (2006.01) | |
| A61K 31/5585 | (2006.01) | |

(52) U.S. Cl.
CPC ........... *A61K 39/3955* (2013.01); *A61K 31/557* (2013.01); *A61K 31/5585* (2013.01); *A61K 31/727* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 2,307,983 | A | 1/1943 | Barnes | |
| 5,549,893 | A * | 8/1996 | Eibl ................ | C07K 16/40 424/94.63 |
| 8,877,710 | B2 * | 11/2014 | Johansson ............ | A61K 31/557 514/13.5 |
| 2004/0023975 | A1 | 2/2004 | Ries et al. | |
| 2004/0067995 | A1 | 4/2004 | Wong et al. | |

FOREIGN PATENT DOCUMENTS

| | | |
|---|---|---|
| WO | 9927962 A1 | 6/1999 |
| WO | 02091719 A2 | 11/2002 |
| WO | 2004000310 A1 | 12/2003 |
| WO | 2006103206 A2 | 10/2006 |
| WO | 2007091719 A1 | 8/2007 |

OTHER PUBLICATIONS

U.S. Appl. No. 13/142,935, filed Jun. 30, 2011.
U.S. Appl. No. 61/161,487, filed Mar. 19, 2009.
Suzuki Y. et al., Integrilin Prevents Prolonged Bleeding Times After Cardiopulmonary Bypass, Ann. Thorac. Surg., 66(2): 373-381, 1998.
Feng et al, Perioperative Paraplegia and Multiorgan Failure From Heparin-Induced Thrombocytopenia, The Annals of Thoracid Surgery 55, 1555-57 (1993).
O'Shea et al, Eptifibatide: A Potent Inhibitor of the Platelet Receptor Integrin, Glycoprotein IIb/III1, Expert Opinion on Investigational Drugs 8, 1893-905 (1999).
Abraham et al., Efficacy and Safety of Tifacogin (Recombinant Tissue Feactor Pathway Inhibitor) in Severe Sepsis, JAMA, Jul. 9, 2003; 290(2):238-347.
Abraham et al., Mechanism of sepsis-induced organ dysfunction. 2007, Grit Care Med., vol. 35, No. 10, pp. 2408-2416.
Afshari et al., Antithrombin III for critically ill patients (Review), Cochrane Database Syst Rev. Jul. 16, 2008; (3): CD005370.
Aird, The role of the endothelium in severe sepsis and multiple organ dysfunction syndrome. 2003, Blood, vol. 101, No. 10, pp. 3765-3777.
Asakura et al., An enhanced fibrinolysis prevents the development of multiple organ failure in disseminated intravascular coagulation in spite of much activation of blood coagulation, 2001, Crit Care Med., vol. 29, No. 6, pp. 1164-1168.
Bernard et al., Efficacy and safety of recombinant human activated protein C for severe sepsis, Crit Care Med. Nov. 2001; 29(11):2051-2059.
Biesalski, Hans Konrad et al., Antioxidant therapy in critical care—is the microcirculation the primary target?, Critical Care Medicine, Williams and Wilkings Company, Baltimore, MA, US, vol. 34, No. 9, Suppl, Sep. 1, 2007, pp. 577-583.
Chung-Hua, Chen E Tal., Fluvastrain attenuate endoxin shock induced organ damage in conscious rats, Resuscitation, vol. 74, No. 1, Jan. 1, 2007, pp. 166-174.
De Meyer et al, Autophagy in the cardiovascular system, Biochimica et Biophysica Acta 1793 (2009), pp. 1485-1495.

(Continued)

*Primary Examiner* — Theodore R West
(74) *Attorney, Agent, or Firm* — Dinsmore & Shohl LLP

(57) ABSTRACT

The present invention relates to compounds for treatment that protects the endothelium, prevents pathologic thrombus formation in the microcirculation and preserves platelet number and function and thus may be related to minimizing or preventing development of organ failure, including multiple organ failure (MOF), and, hence, death in critically ill patients by administration of agent(s) limiting the platelets ability to aggregate and form clots and/or by agents modulating/preserving endothelial integrity and/or by agent(s) increasing the rate of thrombus lysis, and Another aspect of the invention related to by a cell-based whole blood viscoelastical haemostatic assay identifying critically ill patients at increased risk of development of organ failure, including multiple organ failure (MOF) and death.

13 Claims, 4 Drawing Sheets

(56) References Cited

OTHER PUBLICATIONS

De Oliveria et al., Fructose-1, 6-bisphosphate inhibits in vitro and ex vivo platelet aggregation induced by ADP and ameliorates coagulation alterations in experimental sepsis in rats, J Thromb Thrombolysis, Aug. 25, 2009.

Di Paola Rosanna et al., Greene tea polyphenol extract attenuates zymosan-induced non-septic shock in mice, Oct. 2006, shock (Augusta, Ga.) Oct. 2006, vol. 26, No. 4, pp. 402-409.

Ely, E. Wesley et al., Advances in the understanding of clinical manifestations and therapy of servere sepsis: an update for critical care nurses, Mar. 2003, American Journal of Critical Care: an offitial publication, American Association of Critical-care Nurses, Mar. 2003, vol. 12, No. 2, pp. 120-133.

Ganter et al., Coagulation Monitoring: Current Techniques and Clinical Use of Viscoelastic Point-of-Care Coagulation Devices, Anesth Analg. May 2008; 106(5): 1366-1375.

Geerts et al., prevention of Venous Thromboembolism, Chest. Jun. 2008; 133(6 Suppl): 381S-453S.

Goerge et al., Inflammation induces hemorrhage in thrombocytopenia, Blood, May 15, 2008; 111(10): 4958-4964.

Imperatore, Francesco et al., Use of prostacylin in the treatment of sepsis-induced organ failure, Medgenmed: Medscape General Medicine, Webmd Medscape Health network, New York, NY, vol. 5, No. 3, Jul. 31, 2003, p. 15.

Iqbal et al., Antithrombotic agents in the treatment of severe sepsis. 2002, Expert Opin. Emerging Drugs, 7, pp. 111-139.

Kanaan et al., Meta-Analysis of Venous Thromboembolism Prophylaxis in Medically Ill Patients, Clin Ther. Nov. 2007; 29(11):2395-405.

Kozek-Langenecker, Sibylle A. et al., Effect of prostacylin on platelets, polymorphoonuclear cells, and heterotypic cell aggregation during hemofiltration, Critical Care Medicine, Williams and Wilkings Company, Baltimore, MA, US, vol. 31, No. 3, Mar. 1, 2003, pp. 864-868.

Levi and Lowenberg, Thrombocytopenia in Critically Ill Patients, Semin Thromb Hemost 2008; 34(5):417-424.

Marti-Carvajal et al., Human recombinant activated protein C for severe sepsis (Review), Cochrane Database Syst Rev. 2008;(1):CD004388.

Moreau et al., Platelet Count Deline: An Early Prognostic Marker in Critically Ill Patients With Prolonged ICU Stays, Chest 2007; 131(6): 1735-1741.

Nachman and Rafii, Platelets, Petechiae, and Preservation of the Vascular Wall, N. Engl J Med, 2008; 359:1261-1270.

Nguyen and Carcillo, Bench-to-bedside review: Thrombocytopenia-associated multiple organ failure—a newly appreciated syndrome in the critically ill, Critical Care 2006, 10:235, pp. 1-8.

Pontes-Arruda, Alessandro et al., Effects of enternal feeding with eicosapentaenioc acid, gamma-linolenic acid, and antioxidants in mechanically ventilated patients with severe sepsis and septic shock, Critical Care Medicine, Williams and Wilkings Company, Baltimore, MA, US, vol. 34, No. 9, Sep. 1, 2006, pp. 2325-2333.

Pu et al., Beneficial effect of glycoprotein IIb/IIIa inhibitor (AZ-1) on endothelium in *Escherichia coli* endotoxin-induced shocke, 2001, Crit Care med, vol. 29, No. 5, pp. 1181-1188.

Reutershan, Jorg et al., Adenosine and inflammation: DC39 and CD 73 are critical mediators in LPS-induced PMN trafficking into the lungs, Oct. 2008, The Faseb Journal: Official publication of the federation of American Societies for experimental biology Feb. 2009, vol. 23, No. 2, pp. 473-482.

Sagripanti, A., et al., Iloprost in the treatment of thrombotic microangiopathy: report of thirteen cases, Biomedicine and Pharmacotherapy, Elsevier, Paris, FR, LNKD, vol. 50, No. 8, Jan. 1, 1996, pp. 350-356.

Salooja and Perry, Thrombelastography, Blood Coagul Fibrinolysis, Jul. 2001; 12(5):327-337.

Scheeren, T., et al., Proctacyclin (PG12): new aspects of an old substance in the treatment of criticlaly ill patients, Feb. 1997, Intensive Care Medicine, Feb 1997, vol. 23, No. 2, pp. 146-158.

Stephan et al., Thrombocytopenia in a Surgical ICU, Chest. May 1999; 115(5):1363-1370.

Trzeciak, Stephen et al., Clinical manifestations of disordered microcirculatory perfusion in servere sepsis, 2005, Critical Care (London, England) 2005, vol. 9 Suppl. 4, pp. 20-26.

Ueno et al., Coagulation/bigrinolysis abnormality and vascular endothelial damage in the pathogenesis of thrombocytopenic multiple organ failure, 2002, cRIT cARE mED., vol. 30, No. 10, pp. 2242-2248.

Yasuyuki, Suzuki et al., Integrilin Prevents prologed BleedingTimes After Cardiopulmonary Bypass, 1998, The Annals of thoracid surgery, vol. 66, pp. 373-381.

Zardi et al., Endothelial dysfunction and activation as an expression of disease: role of prostacyclin analogs, International immunopharmacology 5 (2005) 437-459.

Zardi et al., prostacyclin in sepsis: A systematic review, Prostaglandins & Other Lipid Mediators 83, 2007, pp. 1-24.

Johansen et al., Profound Endothelial Damage Predicts Impending Organ Failure and Death in Sepsis, Seminars in Thrombosis & Hemostasis, pp. 1-10, New York, NY, USA.

Holmvang et al., A single center, open, randomized study investigating the clinical safety and the endothelial modulating effects of a prostacyclin analog in combination with eptifibatide in patients having undergone primary percutaneous coronary intervention (PCI) for ST-segment elevation myocardial infarction, Prostaglandins & Other Lipid Mediators 99, 2012, pp. 87-95.

\* cited by examiner

P>0,1

P>0,1

P>0,1

P>0,1

P>0,1

METHODS OF IDENTIFYING CRITICALLY ILL PATIENTS AT INCREASED RISK OF DEVELOPMENT OF ORGAN FAILURE AND COMPOUNDS FOR THE TREATMENT HEREOF

CROSS-REFERENCE TO RELATED APPLICATIONS

This application is a divisional of U.S. patent application Ser. No. 13/142,935 filed Jun. 30, 2011, which is the U.S. National Phase of PCT/DK2009/050357 filed Dec. 30, 2009, which claims priority of Danish Patent Application PA 2008 01844 filed Dec. 30, 2008, and U.S. Provisional Application 61/161,487 filed Mar. 19, 2009.

All patent and non-patent references cited in the application, or in the present application, are also hereby incorporated by reference in their entirety.

FIELD OF THE INVENTION

The present invention relates to a novel use of compounds that protect the endothelium, prevent pathologic thrombus formation in the microcirculation and/or preserve platelet number and function in the circulation and thus may be related to minimizing or preventing development of organ failure, including multiple organ failure (MOF), and, hence, death in critically ill patients by administration of agent(s) limiting the platelets ability to aggregate and form clots and/or by agents modulating/preserving endothelial integrity and/or by agent(s) increasing the rate of thrombus lysis, and methods of by a cell-based whole blood viscoelastical haemostatic assay identifying critically ill patients at increased risk of development of organ failure, including multiple organ failure (MOF) and death.

BACKGROUND OF THE INVENTION

Platelets are anucleate fragments of megakaryocyte cytoplasm. They are pivotal for haemostatic plug formation, both by forming the initial thrombus at the site of vascular lesion and by providing template for coagulation protein assembly with subsequent thrombin generation resulting in conversion of fibrinogen to fibrin which interacts with the activated platelets through the GPIIb/IIIa receptor forming the haemostatic clot [Roberts et al. 2006] and by maintaining vascular wall integrity [Nachman and Rafii 2008]

Under physiologic conditions, platelet aggregation and haemostasis is prevented by the vascular endothelium. The endothelium provides a physical barrier and secretes platelet inhibitory products, such as pro stacycline (PGI2) and nitric oxide (NO). These compounds regulate the adhesiveness of platelets and the activation state of the platelet receptor GPIIb/IIIa in a paracrine way and also maintain the endothelium in a quiescent state through autocrine mechanisms [Zardi et al 2005].

With endothelial activation or injury (trauma, critical illness like sepsis, atherosclerosis), platelets adhere to the endothelium or subendothelium, respectively. This adhesion activates platelets, causes a shape change and a release reaction where ADP is released (which is a potent platelet agonist). The platelet membrane integrin receptor, GPIIb/IIIa, becomes activated. Fibrinogen binds to this receptor, effectively cross-linking platelets to form a platelet plug. During platelet activation, thromboxane A2 is formed from hydrolysis of phospholipids (especially phosphatidylcholine) in the platelet membrane. This is an important platelet agonist, recruiting other platelets and activating them, thus promoting further platelet aggregation. Thrombus formation is a problem in many clinical situations, mainly cardiovascular diseases where platelets are also involved in atherothrombotic disease where they support development of thrombus formation on atherosclerotic plaques eventually resulting in occlusion of vessels and cell death, exemplified by acute myocardial infarction [De Meyer et al. 2009].

In Intensive Care Unit (ICU) patients and especially in sepsis, pathologic thrombus formation attributed to inflammation induced endothelial dysfunction and platelet activation is likely to be one of the main causes of morbidity and mortality. Thus, almost half of all patients with sepsis, major trauma or other critical illness present with or develop thrombocytopenia. In critically ill patients, thrombocytopenia upon arrival to the intensive care unit (ICU), is common and is associated with increased mortality [Moreau et al. 2009], longer ICU stays, a higher incidence of bleeding events, greater transfusion requirements and regardless of the cause, thrombocytopenia or declining platelet count is an independent predictor of multi organ failure (MOF) [Nguyen and Carcillo 2006] and ICU mortality [Levi and Lowenberg 2008]. The pathogenesis of low or declining platelet count in critically ill patients is multifactorial and involve e.g., bleeding, sepsis, thrombotic microangiopathy including disseminated intravascular coagulation (DIC) and immune or drug-induced thrombocytopenia [Nguyen and Carcillo 2006; Levi and Lowenberg 2008].

Thrombocytopenia and a decline in platelet count may reflect the same pathophysiologic disturbances seen in sepsis, disseminated intravascular coagulation (DIC), vitamin deficiencies, macrophage activation, drug-induced toxicity, liver disease, haematologic disorders, massive transfusions, immune mediated thrombocytopenia and unidentified factors ref [Moreau et al. 2007]. The increased mortality in critically patients with thrombocytopenia is complex and relates also in part to development of progressive organ failure accompanied by a decline in platelet count, thrombocytopenia associated multi organ failure (TAMOF). TAMOF is a thrombotic microangiopathic syndrome that can be defined by a spectrum of pathology that includes disseminated intravascular coagulation (DIC) and secondary thrombotic microangiopathy (TMA) [Nguyen and Carcillo 2006].

A common feature for TAMOF is the progressive decline in platelet count related to systemic profound coagulation activation, down-regulation of both fibrinolysis and natural anticoagulants resulting in platelet consumption and microvascular thrombus formation where the platelets play an integral role [Nguyen and Carcillo. 2006]. A non-exhaustive list of conditions associated with TAMOF is presented in Table 1.

Table 1: Conditions Associated with Organ Failure, Including MOF and TAMOF

Cancer
Transplantation (solid organs, haematopoietic stem cells)
Cardiovascular surgery/cardiopulmonary bypass/extracorporeal membrane oxygenation (ECMO)
Vascular surgery
Autoimmune disease
Systemic infection
Vasculitis
Exposure to toxins
Cyclosporine A therapy
FK 506 therapy
Chemotherapy
Radiation
Ticlopidine treatment Hemolytic Uremic Syndrome variant syndromes.
Trauma (e.g. polytrauma, neurotrauma, fat embolism)
Non-exhaustive list of conditions associated with TAMOF-DIC is presented in Table 2.
Table 2: Clinical Conditions that May be Associated with Disseminated Intravascular Coagulation
Sepsis/severe infection (any microorganism)
Malignancy
  Myeloproliferative/lymphoproliferative malignancies
  Solid tumors
  Metastasis
Trauma (e.g. blunt/penetrating trauma, polytrauma, neurotrauma, fat embolism, burn trauma)
Obstetrical calamities
  Amniotic fluid embolism
  Abruptio placentae
Organ destruction (e.g. severe pancreatitis)
Severe toxic or immunologic reactions
  Snake bites
  Recreational drugs
  Transfusion reactions
  Transplant rejection (graft vs. host disease, host vs. graft disease)
Vascular abnormalities
  Kasabach-Merritt syndrome
  Large vascular aneuysms
Severe hepatic failure
Embolism
  Thromboembolism
  Cholesterol embolism
  Fat embolism
  Air embolism
  Septic embolism
  Tissue embolism
  Foreign body embolism
  Amniotic fluid embolism Standard treatment in the intensive care unit of critically ill patients with or without thrombocytopenia focuses on:
1. Identification and specific treatment of the underlying disorder causing the patients condition, and
2. support of vital organs in case of failure exemplified by ventilatory support, haemodialysis, vasopressor treatment, parenteral nutrition, fluid support, corticosteroids, tight glycemic control, administration of blood products and others generally referred to as intensive care management [Bick R. 1996, Bick R. 1998].

Furthermore, the treatment may include attenuation of the procoagulant condition by systemic administration of agents which decrease enzymatic coagulation activation such as:
1. Heparins (low molecular weight heparin (LMWH), unfractioned heparin (UFH))
2. Thrombin inhibitors
3. Antithrombin
4. Tissue factor pathway inhibitor (TFPI)
5. Activated Protein C
have been evaluated and especially in critically ill patients with severe sepsis which carries a high mortality (>50%).

Ad 1. Heparins
Meta-analysis suggests that venous thromboembolism (VTE) prophylaxis with an LMWH (including fondaparinux) or UFH is effective in reducing the rate of deep venous thrombosis (DVT), but this benefit did not extend to enhanced protection against pulmonary embolism (PE). Additionally, LMWH and UFH had similar bleeding outcomes and hence VTE prophylaxis with heparins is standard therapy in critically ill medical and surgical patients, also in the ICU. It is recommended that, on admission to the ICU, all patients are assessed for their risk of VTE, and that most receive thromboprophylaxis (Grade 1A) [Kanaan et al. 2007, Geerts et al. 2008].

Ad 2. Thrombin Inhibitors
Direct thrombin inhibitors (DTIs) act as anticoagulants (delaying blood clotting) by directly inhibiting the enzyme thrombin. There are two types of DTIs, dependent on their interaction with the thrombin molecule. Bivalent DTIs (hirudin and analogs) bind both to the active site and exosite 1, while univalent DTIs bind only to the active site. Bivalent: Hirudin, Bivalirudin, Lepirudin, Desirudin; Univalent: Argatroban, Melagatran, Dabigratan Ad 3. Antithrombin
A Cochrane analysis included 20 randomized trials with a total of 3458 participants; 13 of these trials had high risk of bias. When combining all trials, AT III did not statistically significantly reduce overall mortality compared with the control group (RR 0.96, 95% CI 0.89 to 1.03; no heterogeneity between trials). A total of 32 subgroup and sensitivity analyses were carried out. Analyses based on risk of bias, different populations, and the role of adjuvant heparin gave insignificant differences. AT III reduced the multiorgan failure score among survivors in an analysis involving very few patients. AT III increased bleeding events (RR 1.52, 95% CI 1.30 to 1.78). ATIII therapy of critically ill patients is not recommended [Afshari et al. 2008].

Ad 4. TFPI
Efficacy and safety of tifacogin (recombinant tissue factor pathway inhibitor) in severe sepsis was evaluated in a randomized controlled trial (OPTIMIST) encompassing 1754 patients. All cause mortality in the TFPI treated group was 34.2% vs 33.9% in placebo treated patients, p=0.88. Tifacogin administration was associated with an increase in risk of bleeding, irrespective of baseline INR and there is currently no indication for TFPI treatment of patients with severe sepsis [Abraham et al. 2003].

Ad 5. Activated Protein C
The PROWESS study in patients with severe sepsis was prematurely stopped at the second interim analysis because of a significant reduction in mortality in the APC treated patients [Bernard et al 2001]. A total number of 1728 patients were included and randomized in this study, of which 1690 were eligible for analysis. Of these patients, 840 were randomized to receive recombinant human APC at a dose of 24 mg/kg/h for 96 h, and 850 patients received placebo. Mortality was 24.7% in the APC group as compared with 30.8% in the placebo group (relative risk reduction 19.4 percentages, 95% confidence interval 6.6-30.5). The series of negative trials in specific populations of patients with severe sepsis performed after the PROWESS study has added to the scepticism regarding the use of APC [Marti-Carvajal et al. 2007]. Furthermore, on the basis of the ADDRESS study, treatment with APC seems not to be indicated in patients with sepsis and a relatively low disease severity [Levi M 2008]. No consensus regarding the use of APC in patients with severe sepsis exists today.

Despite all these initiatives, many patients do not achieve homeostasis, continue to bleed, become immunodeficient, loose endothelial wall integrity (the endothelial wall becomes activated), and/or develop MOF and/or TAMOF and die. Thus, there remains a need for a method of treatment for critically ill patients; a method which may include treatment and/or prevention of development of organ failure such as MOF and/or TAMOF, and/or arrest bleeding, and/or prevent immunodeficiency, and/or preserving endothelial integrity in critically/acutely ill patients and furthermore, there is a need for a composition that may be used in this method.

BRIEF DESCRIPTION OF THE INVENTION

Surprisingly, the present inventors have found that the administration of a combination of a platelet inhibitor and at least one other compound, the at least one other compound being selected amongst a compound capable of modulating/preserving the endothelial integrity, a compound capable of augmenting the fibrinolytic activity, or a TAFIa inhibitor is beneficial in the treatment and/or prevention of organ failure, wherein organ failure is defined as altered organ function in an acutely ill patient. The patient may require medical intervention to achieve homeostasis; and organ failure includes as used herein MOF and TAMOF, in at least one organ, such as in at least two, three, four or five organs.

Furthermore, a combination of compounds that target both the platelets and endothelium to obtain a synergistic effect of the compounds as compared to only targeting either the platelets or the endothelium is an aspect of the present invention. Also, it is an aspect that by combining the treatments, a lower level/dosage of the compound(s) to be administered may be required with the advantage of reduced risk of possible adverse events.

The theory behind the current invention is that thrombocytopenia and/or declining platelet count in critical illness:
1. Is a consequence of enhanced platelet activation, aggregation and thrombus formation in the microvasculature and hence a strong marker of increased risk of microthrombi-ischemia-induced organ failure and/or
2. Induces endothelial dysfunction through lack of and/or dysregulated paracrine effects of platelets released mediators on endothelial integrity and/or activation state and/or
3. Results in immunodeficiency through an integrated effect of platelets on cells of the innate and adpative immune system and hence on the inflammatory response.

The thrombocytopenia observed in many ICU patients is thus a marker and/or driver of profound dysregulation attributed to exaggerated microthrombi formation, endothelial activation, dysfunction and integrity loss and immunodeficiency through compromised platelet function on a per cell basis and through a general reduction in platelets mass, all contributing to pathologies, exemplified by organ failure, in ICU patients.

As stated above, the inventors propose that thrombocytopenia per se results in immunodeficiency through loss of platelet-mediated immune functions. Due to significant redundancy, the thrombocytopenia associated immunodeficiency (TAID) may be aggravated when other limbs of the immune system are compromised, as in critically ill patients. TAID in critical illness may thus in part explain the negative predictive value of low or declining platelet count and the administration of the compounds, combinations of same and pharmaceutical compositions described herein may also be beneficial to this novel aspect of thrombocytopenia.

Under physiologic conditions, platelet aggregation and haemostasis is prevented by the vascular endothelium. The endothelium provides a physical barrier and secretes platelet inhibitory products, such as prostacyclin (PGI2) and nitric oxide (NO). These compounds regulate the adhesiveness of platelets and the activation state of the platelet receptor GPIIb/IIIa in a paracrine way and also maintain the endothelium in a quiescent state through autocrine mechanisms [Zardi et al 2005]. Without being bound by theory it is suggested that preservation of normal circulating platelet count may protect against bleeding alone through these paracrine mechanisms, despite concomitant direct inhibition of platelet aggregation and clot formation [Goerge et al. 2008.]

The present invention relates in a first aspect to pharmaceutical compositions comprising one or more of any of the compounds mentioned herein below, such as one compound, such as at least two compounds, such as at least three compounds. When using more than one compound, the compounds may be selected from the same group of compounds, or more preferably the at least two compounds may be selected from different groups of compounds. Accordingly, in one embodiment one compound is a platelet inhibitor and the at least one other compound is a compound capable of modulating/preserving the endothelial integrity, a compound capable of augmenting the fibrinolytic activity, or a TAFIa inhibitor. In another embodiment, one compound is a compound capable of modulating/preserving the endothelial integrity and the at least one other compound is a compound capable of augmenting the fibrinolytic activity, or a TAFIa inhibitor. In a third embodiment one compound is a compound capable of augmenting the fibrinolytic activity and the at least one other compound is a TAFIa inhibitor.

Preferably the one or more compounds are a platelet inhibitor and a compound capable of modulating/preserving the endothelial integrity, more preferably an antithrombotic compound even more preferably a GPIIb/IIIa inhibitor and PGI2.

Another aspect of the invention relates to the use of a pharmaceutical composition as described herein for treatment and/or prevention organ failure wherein organ failure is defined as altered organ function in an acutely ill patient requiring medical intervention to achieve homeostasis; organ failure includes as used herein MOF and TAMOF, in at least one organ, such as in at least two, three, four or five organs.

Still another aspect of the invention relates to the use of the pharmaceutical composition as described herein for prevention or treatment of organ failure wherein organ failure is defined as altered organ function in an acutely ill patient requiring medical intervention to achieve homeostasis; organ failure includes as used herein MOF and TAMOF, in at least one organ, such as in at least two, three, four or five organs wherein the organs are selected from the group consisting of cardiovascular, respiratory, renal, haematological, neurological, gastrointestinal and hepatic organs.

Another aspect of the invention relates to a composition comprising one or more compounds selected from the group consisting of platelet inhibitors, compounds capable of modulating/preserving the endothelial integrity, compounds capable of augmenting the fibrinolytic activity, or TAFIa inhibitors for use in treatment and prevention of organ failure wherein organ failure is defined as altered organ function in an acutely ill patient requiring medical intervention to achieve homeostasis; organ failure includes as used herein MOF and TAMOF, in at least one organ, such as in at least two, three, four or five organs.

Another aspect of the invention relates to a composition comprising a platelet inhibitor and a compound capable of modulating/preserving endothelial integrity for use in the treatment and prevention of organ failure wherein organ failure is defined as altered organ function in an acutely ill patient requiring medical intervention to achieve homeostasis; organ failure includes as used herein MOF and TAMOF, in at least one organ, such as in at least two, three, four or five organs.

Another aspect of the invention relates to a composition comprising one or more compounds selected from the group consisting of platelet inhibitors, compounds capable of modulating/preserving the endothelial integrity, compounds capable of augmenting the fibrinolytic activity, or TAFIa inhibitors for use in treatment and prevention of organ failure wherein organ failure is defined as altered organ function in an acutely ill patient requiring medical intervention to achieve homeostasis; organ failure includes as used herein MOF and TAMOF, in at least one organ, such as in at least two, three, four or five organs.

Yet another aspect of the invention relates to a composition comprising a platelet inhibitor and a compound capable of modulating/preserving endothelial integrity for use in the treatment and prevention of organ failure wherein organ failure is defined as altered organ function in an acutely ill patient requiring medical intervention to achieve homeostasis; organ failure includes as used herein MOF and TAMOF, in at least one organ, such as in at least two, three, four or five organs.

Another aspect of the invention relates to a compound as described herein or a composition as described herein for prevention or treatment of organ failure, wherein organ failure is defined as altered organ function in an acutely ill patient requiring medical intervention to achieve homeostasis; organ failure includes as used herein MOF and TAMOF, in at least one organ, such as in at least two, three, four or five organs, wherein the organ failure is due to systemic inflammation or due to severe infections or due to sepsis or due to systemic inflammatory response syndrome (SIRS) and/or compensatory anti-inflammatory response syndrome CARS or due to coagulopathy or due to trauma and/or burns or due to malignant diseases such as haematological malignancies, solid tumours and metastatic tumours or due to ischemia or due to cardiovascular thromboembolic diseases or due to intoxication.

In a further aspect the invention relates to one or more platelet inhibitors for prevention or treatment of organ failure wherein organ failure is defined as altered organ function in an acutely ill patient requiring medical intervention to achieve homeostasis; organ failure includes as used herein MOF and TAMOF, in at least one organ, such as in at least two, three, four or five organs.

In a particular embodiment the organ failure is due to sepsis or due to malignant diseases such as solid tumours, haematological malignancies and metastatic tumours or the systemic inflammatory response syndrome and compensatory anti-inflammatory response syndrome, accompanying trauma.

In a further particular embodiment the organ or organs, which are subject to failure are selected from the group consisting of cardiovascular, respiratory, renal, haematological, neurological, gastrointestinal and hepatic organs, such as heart, liver, lungs, gut, kidneys, spleen, and brain.

In a still further aspect the invention relates to a one or more compounds capable of modulating/preserving endothelial integrity for prevention or treatment of organ failure wherein organ failure is defined as altered organ function in an acutely ill patient requiring medical intervention to achieve homeostasis; organ failure includes as used herein MOF and TAMOF, in at least one organ, such as in at least two, three, four or five organs.

A further aspect of the invention relates to a method of treating or preventing organ failure, including multi organ failure, defined as altered organ function in an acutely ill patient requiring medical intervention to achieve homeostasis; organ failure includes as used herein MOF and TAMOF comprising administering one or more compounds selected from the group consisting of platelet inhibitors, compounds capable of modulating/preserving the endothelial integrity, compounds capable of augmenting the fibrinolytic activity, or TAFIa inhibitors.

Another aspect of the invention relates to the use of one or more compounds selected from the group consisting of platelet inhibitors, compounds capable of modulating/preserving the endothelial integrity, compounds capable of augmenting the fibrinolytic activity, or TAFIa inhibitors in the manufacture of a medicament for the treatment or prevention of organ failure, including multi organ failure, defined as altered organ function in an acutely ill patient requiring medical intervention to achieve homeostasis; organ failure includes as used herein MOF and TAMOF.

Another aspect of the invention relates to a pharmaceutical composition for treating or preventing organ failure, including multi organ failure, defined as altered organ function in an acutely ill patient requiring medical intervention to achieve homeostasis; organ failure includes as used herein MOF and TAMOF comprising one or more compounds selected from the group consisting of platelet inhibitors, compounds capable of modulating/preserving the endothelial integrity, compounds capable of augmenting the fibrinolytic activity, or TAFIa inhibitors as an active ingredient.

In another particular embodiment the organ failure is due to reperfusion injury following ischemia.

In another aspect the invention relates to a compound capable of augmenting the fibrinolytic activity in whole blood for prevention or treatment of organ failure, wherein organ failure is defined as microthrombosis in at least one organ, such as in at least two, three, four or five organs.

In yet another aspect the invention relates to a thrombin activatable fibrinolysis inhibitor (TAFI) an inhibitor for prevention or treatment of organ failure, wherein organ failure is defined as microthrombosis in at least one organ, such as in at least two, three, four or five organs.

A further aspect relates to the use of a combination of compounds and/or compositions as herein described for treatment of critically ill patients by the preservation of platelet count, whereby the patient suffers less risk of becoming immunodeficient.

Thus the use of the pharmaceutical composition as herein disclosed for the preservation of platelet number and/or function in a critically ill patient requiring medical intervention to achieve homeostasis is also an aspect of the present invention.

Another aspect of the present invention relates to the use of the compounds and/or compositions as herein described for immunostimulating purposes, the immunostimulation being direct and/or indirect.

Yet another aspect of the invention relates to a method of diagnosing, monitoring or determining the likelihood of a organ failure including multi organ failure (MOF) in a critical ill human being, wherein said method is capable of identifying critical ill human beings who have a significantly increased risk of developing organ failure, including MOF, said method comprising the steps of i) determining at least one of the viscoelastical values R, Angle and MA by thromboelastography (TEG) or equivalent parameters identified by thromboelastometry in a whole blood sample from the human being critically ill, such as in a citrated whole blood sample, such as in a citrated whole blood sample activated by kaolin, such as in a citrated whole blood sample activated by tissue factor, such as in a native whole blood sample, such as a native whole blood sample activated by kaolin, such as in a citrated whole blood sample activated by tissue factor ii) comparing said value with a predetermined cutoff value, said cutoff value being an equivalent to a cutoff value determined by TEG in a citrated whole blood sample activated by kaolin wherein said cutoff value is a) R higher than 8.0 minutes, such as higher than 8.5 minutes, or lower than 4.0 minutes, such as lower than 3.0 minutes, b) Angle lower than 55°, such as lower than 52°, or higher than 78°, such as higher than 80°, and c) MA lower than 51 mm, such as lower than 50 mm, or higher than 69 mm, such as higher than 72 mm wherein an R-value higher or lower than the cutoff value and/or an Angle-value higher or lower than the cutoff value and/or a MA higher or lower than the cutoff value is indicative of a significantly increased risk of developing organ failure as compared to a human being wherein neither R, Angle-value or MA is higher or lower than the cutoff value.

The method allows for the identification of critically ill patients with a significantly increased risk of development organ failure, including MOF, and 30-day mortality earlier than conventional coagulation analyses exemplified by activated partial thromboplastin time (APTT), prothrombin time (PT), platelet count and D-dimer.

Additional aspects of the present invention and particular embodiments will be apparent from the description below, as well from the appended claims.

DETAILED DESCRIPTION OF THE INVENTION

Figure 1:
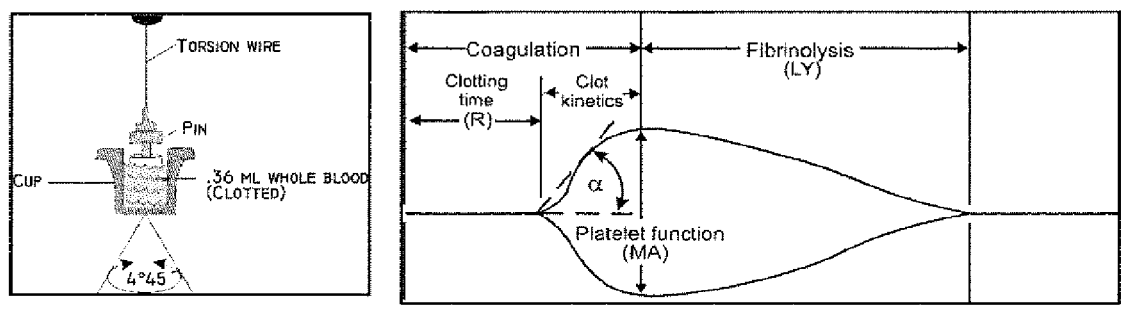
FIG. 1: Recording haemostatic activity using TEG assay.

Interventions aiming at reducing/inhibiting the platelets ability to participate in the clot building process (eg. the administration of platelet inhibitors) will prohibit or reduce development of thrombus formation in the microvasculature and therefore reduce endothelial activation, will increase, preserve and/or reduce the fall in the circulating platelet count and therefore improve endothelial integrity and/or limit and/or avoid thrombocytopenia associated immunodeficiency and hence, limit and/or prevent development of organ failure including MOF.

Furthermore, interventions aiming at modulating/preserving endothelial integrity (keeping the endothelium in a quiescent inactivated anti-coagulant state, eg. by the administration of endothelial modulators) will reduce endothelial activation and improve endothelial integrity and therefore prohibit and/or reduce development of thrombus formation in the microvasculature which will increase and/or preserve circulating platelet count and avoid thrombocytopenia associated immunodeficiency and hence, limit and/or prevent development of organ failure including MOF.

Also, interventions aiming at increasing the fibrinolysis (eg. the administration of pro-fibrinolytics) will reduce clot stability through enhanced fibrinolysis and thereby reduce or prohibit development of thrombus formation in the microvasculature and therefore, through the above mentioned effects on endothelial cells and immune function, limit and/or prevent development of organ failure including MOF.

In addition, interventions aiming at reducing the activity of TAFIa (eg. the administration of TAFIa-inhibitors) will reduce clot stability through enhanced fibrinolysis and thereby reduce or prohibit development of thrombus formation in the microvasculature and therefore, through the above mentioned effects on endothelial cells and immune function, limit and/or prevent development of organ failure, including MOF.

Finally, interventions aiming at reducing/inhibiting the platelets ability to participate in the clot building process (platelet inhibitors) and/or modulating/preserving endothelial integrity (endothelial modulators) and/or increasing the fibrinolytic activity (pro-fibrinolytics) and/or reducing the activity of TAFIa (TAFIa-inhibitors) in any combination will reduce clot stability and thereby reduce or prohibit development of thrombus formation in the microvasculature and therefore, through the above mentioned effects on endothelial cells and immune function, limit and/or prevent development of organ failure including MOF.

Accordingly, the present invention relates to compounds for a new treatment modality for critically ill patients, in particular patients having acquired or at increased risk of development of organ failure, including MOF, such as TAMOF or any condition associated with systemic inflammation.

Given the above mentioned association between critical illness with imminent or manifest organ failure and platelet activation and/or loss, endothelial activation and/or dysregulation and immunodeficiency and/or dysregulation, interventions that simultaneously 1. Modulate and/or preserve endothelial integrity by keeping the endothelium in a quiescent inactivated anti-coagulant state (endothelial modulators, described herein below); and
2. Reduce and/or inhibit the platelets ability to participate in the clot building process (platelet inhibitors, described herein below); or
3. Enhance fibrinolysis and thereby dissolve already formed microthrombi or prevent formation of microthrombi in the microcirculation (pro-fibrinolytics); or
4. Inhibit thrombin-activatable fibrinolysis inhibitor (TAFI)a and thereby enhance fibrinolysis (TAFIa-inhibitors)

should be used to prevent and/or cure imminent and/or manifest organ failure and/or serve to induce/preserve homeostasis in critically ill patients. These patients may have any condition associated with systemic inflammation (conditions suitable for the invention, described herein below).

A further aspect relates to preserving/upholding the platelet count and/or platelet function in a subject/patient. The patient may be a critically ill patient. Such a patient may be in the need of medical intervention to achieve homeostasis. By preserving the platelet count, the competency of the platelets as immunocompetent cells is preserved and the immunodeficiency typically observed in patients and especially in critically ill patients is hereby avoided. By upholding or preserving the platelet count is understood an action that aims at maintaining the platelet count within normal levels ie. a level above a level defined as thrombocytopenic and below a level indicative of thrombocytosis. Thus the level may be a level such as in a healthy individual wherein a normal platelet count ranges from 150,000 and 450,000 per mm$^3$ (or microlitre) (150-450×10$^9$/L). These limits, however, are determined by the 2.5th lower and upper percentile, and a deviation does not necessary imply any form of disease nor alleviate the need for treatment as herein proposed. Administering the herein disclosed compounds or combinations/compositions comprising the same will have the effect of preserving the platelet count in an individual in need hereof. As follows here from, the individual will thus be receiving an immunostimulating treatment. The immunostimulating treatment will be by indirect immunostimulation as it regards the number/function of the platelets.

It is thus an object of the present invention that the herein disclosed compounds, combinations hereof and compositions comprising these compounds are for use in the treatment of immunodeficiency and/or thrombocytopenia and/or critical illness and/or for use as (indirect) immunostimulating compounds/compositions. These compounds and compositions are to the preservation of platelet counts within normal levels in subjects in need there of, such subjects include subjects suffering from immunodeficiency and/or in need of immuno stimulation and/or subjects suffering from critical illness.

It follows that the compound and compositions of the present invention may be used for immunotherapy, especially activating immunotherapy which is defined as treatment of a condition or a disease by inducing and/or enhancing an immune response.

Therefore an object of the present invention relates to the use of the pharmaceutical compositions herein disclosed for the preservation of platelet number and/or function. The recipient of the treatment may be a critically ill patient requiring medical intervention to achieve homeostasis.

In a further aspect the present invention relates to a method of diagnosing critically ill patients at increased risk of development of organ failure, including MOF, such as TAMOF, employing a viscoelastical citrated whole blood assay, such as TEG analysis, upon arrival to the ICU, for those patients presenting either with a hypocoagulable TEG, defined as a cut-off value wherein (when using Kaolin activated citrated whole blood) a R higher than 8 minutes, such as 8.5 minutes or higher, and/or MA lower than 51 mm, such as lower than 50 mm and/or Angle lower than 55°, such as lower than 52° or a hypercoagulable TEG defined as R lower than 4.0 minutes, such as lower than 3.0 minutes, angle higher than 80°, and MA higher than 69 mm, such as higher than 72 mm.

Definitions

The term "antiaggregatory" is intended to mean a lower than normal ability of the platelets to interact in the clot building process secondary to administration of compounds and/or variants that inhibit the platelets ability to aggregate [Kawasaki et al 2007, Fries et al. 2006, Velik-Salchner et al. 2007, Bassus et al. 2006, Tomokiyo et al. 2003].

The term "antithrombotic" is also intended to mean a lower than normal ability of the platelets to interact in the clot building process secondary to administration of compounds and/or variants that inhibit and/or decreases the platelets ability to aggregate and inhibit the platelets ability to form clots (thrombus formation).

The terms "antiaggregatory" and "antithrombotic" is used interchangeably and refers to the effect of compound(s) that reduces the platelets ability to interact in the clot building process and hence form thrombi.

The term "modulating/preserving endothelial integrity" is intended to mean pharmacological treatment aiming at maintaining the endothelium in a quiescent inactivated anti-coagulant state. Thus a "compound capable of modulating/preserving endothelial integrity" is intended to mean any compound that may assist in maintaining/inducing the endothelium in a quiescent inactivated anti-coagulant state.

The term "fibrinolytic activity" or fibrinolysis is intended to mean process wherein a fibrin clot, the product of coagulation, is broken down.

The term "augmenting fibrinolytic activity" is intended to mean pharmacological treatment aiming at augmenting the break down of fibrin clots.

The term "hypocoagulability" used herein will reflect a slower initiation phase (increased R), and/or reduced thrombin burst (decreased Angle) and/or reduced clot strength (reduced MA) as evaluated by TEG as compared to the normal reference.

The term "hypercoagulability" used herein will reflect an increased coagulation activity in the initiation phase (decreased R), and/or increased thrombin burst (increased Angle) and/or increased clot strength (increased MA) as evaluated by TEG as compared to the normal reference.

The term "homeostasis" refers to the body's ability to regulate physiologically its inner environment to ensure its stability. An inability to maintain homeostasis may lead to death or a disease.

The term "Organ Failure" is altered organ function in an acutely ill patient requiring medical intervention to achieve homeostasis; organ failure includes as used herein Multi Organ Failure "MOF" and Thrombocytopenia Associated Multi Organ Failure "TAMOF".

The term "MOF" (Multi Organ Failure) is altered organ function in an acutely ill patient requiring medical intervention to achieve homeostasis; MOF includes as used herein TAMOF. MOF is also known as Multiple organ dysfunction syndrome (MODS).

The term "TAMOF" (Thrombocytopenia Associated Multi Organ Failure) used herein will reflect any condition affecting critically ill patients related to development of multiorgan failure secondary to a pathological consumption of platelets resulting in thrombus formation in the microcirculation either due to thrombotic microangiopathic disease or secondary to disseminated intravascular coagulation or any other condition associated with a decline in platelet count and/or function.

The term "TAID" (thrombocytopenia associated immunodeficiency) used herein refers to a defective immunologic competence and/or dysregulated inflammatory response resulting in increased risk of acquiring an infection, dissemination of an established infection and/or excessive dysregulated inflammation with accompanying increased morbidity and mortality.

The term "critically ill", herein also acutely ill, is meant to include any condition rendering the patient in need for intensive care therapy. Intensive care therapy may include but is not limited to induction of homeostasis, ventilation (eg. mechanical ventilation), haemodialysis, vasopressor support, fluid support, parenteral nutrition, administration of red blood cell concentrates, fresh frozen plasma, platelet concentrates, whole blood, systemic antibiotic and/or antiviral and/or antifungal and/or antiprotozoic therapy, granulocyte infusion, T cell infusion, stem cell infusion, anticoagulant therapy including but not limited to administration of activated protein C and/or antithrombin and/or TFPI and/or heparins, including low molecular weight heparins, and/or thrombin inhibitors, administration of corticosteroids, tight glycemic control.

A "subject" includes humans and other mammals, and thus the methods are applicable to both human therapy and veterinary applications, in particular to human therapy. The term "mammal" includes humans, non-human primates (e.g. baboons, orangutans, monkeys), mice, pigs, cows, goats, cats, dogs, rabbits, rats, guinea pigs, hamsters, horse, monkeys, sheep or other non-human mammal.

"Treatment", as used in this application, is intended to include both prevention of an expected development or treatment of an established organ failure, including MOF. Four classes of compounds are envisaged as beneficial for this purpose:

"Reperfusion injury" as used herein refers to damage to tissue caused when blood supply returns to the tissue after a period of ischemia. The absence of oxygen and nutrients from blood creates a condition in which the restoration of circulation results in inflammation and oxidative damage through the induction of oxidative stress rather than restoration of normal function.

The term "systemic inflammation" is altered organ function in an acutely ill patient due to the nonspecific conserved response of the body (vasculature, immune system, tissues) to infections, non-infectious antigens, trauma, burn, organ/tissue destruction/degeneration/damage, ischemia, haemorrhage, intoxication, and/or malignancy.

"Sepsis" as used herein is intended to refer to whole-body inflammatory state (called a systemic inflammatory response syndrome or SIRS) and the presence of a known or suspected infection. Severe sepsis occurs when sepsis leads to organ dysfunction, low blood pressure (hypotension), or insufficient blood flow (hypoperfusion) to one or more organs (causing, for example, lactic acidosis, decreased urine production, or altered mental status). Sepsis can lead to septic shock, multiple organ dysfunction syndrome/multiple organ failure, and death. Organ dysfunction results from sepsis-induced hypotension (<90 mmHg or a reduction of ≥40 mmHg from baseline) and diffuse intravascular coagulation, among other things.

Examples of end-organ dysfunction include the following:
Lungs
   acute lung injury (ALI) ($PaO_2/FiO_2$<300) or acute respiratory distress syndrome (ARDS) ($PaO_2/FiO_2$<200)
Brain
   encephalopathy
     symptoms:
       agitation
       confusion
       coma
     etiologies:
       ischemia
       hemorrhage
       microthrombi
       microabscesses
       multifocal necrotizing leukoencephalopathy
Liver
   disruption of protein synthetic function: manifests acutely as progressive coagulopathy due to inability to synthesize clotting factors
   disruption of metabolic functions: manifests as cessation of bilirubin metabolism, resulting in elevated unconjugated serum bilirubin levels (indirect bilirubin)
Kidney
   oliguria and anuria
   electrolyte abnormalities
   volume overload
Heart
   systolic and diastolic heart failure, likely due to cytokines that depress myocyte function
   cellular damage, manifest as a troponin leak (although not necessarily ischemic in nature)

"SIRS" or systemic inflammatory response syndrome as used herein is intended to mean systemic inflammation in response to an insult without confirmed infectious process. When an infection is suspected or proven (by culture, stain, or polymerase chain reaction (PCR)), together with SIRS, this is per definition sepsis. Specific evidence for infection includes WBCs in normally sterile fluid (such as urine or cerebrospinal fluid (CSF), evidence of a perforated viscus (free air on abdominal x-ray or CT scan, signs of acute peritonitis), abnormal chest x-ray (CXR) consistent with pneumonia (with focal opacification), or petechiae, purpura, or purpura fulminans "Trauma" as used herein is intended to mean any body wound or shock produced by sudden physical injury, as from accident, injury, or impact.

Embodiments

As described herein above, a main aspect of the invention relates to compounds for treatment that protects the endothelium, prevent pathologic thrombus formation in the microcirculation and preserve platelet number and function and thus may be related to minimizing or preventing development of organ failure, including multiple organ failure (MOF), and, hence, death in critically ill patients by administration of compound(s) limiting the platelets ability to aggregate and form clots and/or by agents modulating/preserving endothelial integrity and/or by agent(s) increasing the rate of thrombus lysis, and pharmaceutical compositions comprising one or more of any of the compounds mentioned.

Said compounds are preferably antithrombotic compounds and are more preferably selected from one or more of the groups described herein below.

Antithrombotic Compounds
   1. Platelet inhibitors
   2. Agents modulating/preserving endothelial integrity
   3. Pro-fibrinolytic compounds
   4. Inhibitors against TAFIa Antithrombotic compounds belonging to the four different groups are disclosed below. It is envisaged that more than one compound from each of the four classes may be administered to a person in need thereof for the prevention or treatment of organ failure, including MOF, in particular TAMOF in critically ill patients and patients with systemic inflammation. In a particular embodiment at least two compounds from at least two of the different classes listed above or one compound from one of the different classes listed above are administered to a person in need thereof for the prevention or treatment of critical illness, systemic inflammation, organ failure, including MOF, in particular TAMOF.

In the following, names of compounds of relevance for the present invention are listed. Trade names covering any of the herein mentioned compounds are also of relevance for the present invention.

Platelet Inhibitors

Platelet inhibitors are compounds that interfere with platelet activation (including adhesion, secretion), aggregation and ultimate platelet-fibrin clot formation. Consequently, platelet activation including secretion of alpha, dense, lysosomal and other granules are reduced or inhibited. Also, exposure of negatively charged phosphatidylserine on the platelet surface is reduced or inhibited. Furthermore, activation of the GPIIb/IIIa receptor, being the final common pathway for activation by the thromboxane receptor, ADP receptor and PAR receptors is prevented or limited. In addition, exposure several platelet receptors and/or molecules are reduced or inhibited.

Any agent that reversibly or irreversibly reduces and more preferably inhibits platelet activation/aggregation by blocking sites on the platelet surface or capable of intracellular inhibition can be used as the platelet inhibitor in the present invention.

Platelet inhibitors according to present invention may include any agent that is intended to be used as an antithrombotic or antiaggregatory agent. Any agent that reversibly or irreversibly reduces and more preferably inhibits platelet activation/aggregation by blocking sites on the platelet surface or capable of intracellular inhibition of pathways that mediates platelet activation can be used as the platelet inhibitor in the present invention.

A non-exhaustive list of examples of platelet inhibitors for the prevention or treatment of organ failure including MOF and TAMOF in critically ill patients and/or patients with systemic inflammation encompass the following:

1. Compounds inhibiting the platelet GPIIb/IIIa receptor such as: abciximab, eptifibatide, tirofiban, orbofiban, xemilofiban, lamifiban, XJ757, DUP728, XR299, linear or novel cyclic RGD peptide anlogs, cyclic petides, peptidomimetics inhibiting this receptor and the like, and mixtures hereof and other compounds.

In a particular embodiment the compound inhibiting the platelet GPIIb/IIIa receptor is administered together with a prostacyclin or a prostacyclin analog, see below.

2. Compounds inhibiting the platelet ADP receptor (P2Y12) such as: AR-C69931 MX, Ticlopidine, Clopidogrel, Prasugrel, AZD6140, cangrelor, ticagrelor and other compounds inhibiting this receptor.

In a particular embodiment the compound inhibiting the platelet ADP receptor (P2Y12) is administered together with a prostacyclin or a prostacyclin analog, see below.

3. Compounds inhibiting the platelet P2Y1 receptor such as: MRS2500, MRS2298, MRS2496, A2P5P, A3P5P, ATP, 2-MeSATP, and 2-ClATP.

In a particular embodiment the compound inhibiting the platelet receptor (P2Y1) is administered together with a prostacyclin or a prostacyclin analog, see below.

4. Compounds inhibiting the platelet COX1 and/or COX2 pathways such as
   a. COX inhibitors which have the ability to inhibit as well COX1 as COX2, such as
      i. Salicylates selected from the group consisting of Acetylsalicylic acid (Aspirin), Amoxiprin, Benorylate/Benorilate, Choline magnesium salicylate, Diflunisal, Ethenzamide, Faislamine, Methyl salicylate, Magnesium salicylate, Salicyl salicylate and Salicylamide;
      ii. Arylalkanoic acids selected from the group consisting of Diclofenac, Aceclofenac, Acemethacin, Alclofenac, Bromfenac, Etodolac, Indomethacin, Nabumetone, Oxametacin, Proglumetacin, Sulindac and Tolmetin;
      iii. 2-Arylpropionic acids (profens) selected from the group consisting of Ibuprofen, Alminoprofen, Benoxaprofen, Carprofen, Dexibuprofen, Dexketoprofen, Fenbufen, Fenoprofen, Flunoxaprofen, Flurbiprofen, Ibuproxam, Indoprofen, Ketoprofen, Ketorolac, Loxoprofen, Naproxen, Oxaprozin, Pirprofen, Suprofen and Tiaprofenic acid;
      iv. N-Arylanthranilic acids (fenamic acids) selected from the group consisting of Mefenamic acid, Flufenamic acid, Meclofenamic acid and Tolfenamic acid;
      v. Pyrazolidine derivatives selected from the group consisting of Phenylbutazone, Ampyrone, Azapropazone, Clofezone, Kebuzone, Metamizole, Mofebutazone, Oxyphenbutazone, Phenazone and Sulfinpyrazone;
      vi. Oxicams selected from the group consisting of Piroxicam, Droxicam, Lornoxicam, Meloxicam and Tenoxicam;
   b. COX inhibitors which are specific for inhibition of COX2 such as Celecoxib, Etoricoxib, Lumiracoxib, Parecoxib, Rofecoxib, Valdecoxib, Nimesulide, Licofelone and Omega-3 fatty acids.

In a particular embodiment the compound inhibiting COX is administered together with a prostacyclin or a prostacyclin analog, see below 5. Compounds inhibiting thromboxane-synthase (TX-synthase) such as flavonoids and thromboxane receptor (TP)-antagonists, such as SQ29548, Bay u 3405, or BM 13.177.

In a particular embodiment the compound inhibiting thromboxane-synthase (TX-synthase) and/or thromboxane receptor (TP)-antagonists is administered together with a prostacyclin or a prostacyclin analog, see below.

6. Compounds inhibiting adenosine uptake in the platelets such as dipyramidol, Persantin, Asasantin, Aggrenox and other compounds with a similar mode of action.

In a particular embodiment the compound inhibiting adenosine uptake in the platelets is administered together with a prostacyclin or a prostacyclin analog, see below.

7. Compounds inhibiting the platelet GPIb receptor, such as mAB Ib-23, mAB 6B4, R9alpha557 peptide, aurintricarboxylic acid (ATA), crotalin, agkistin, peptide (Trp-Ile-Arg-Arg-Pro-Phe-Phe-Pro-Phe) from alpha B-crystallin.

In a particular embodiment the compound inhibiting the platelet GPIb receptor is administered together with a prostacyclin or a prostacyclin analog, see below.

8. Compounds inhibiting the platelet GPVI receptor, such as EXP3179, triplatin-1 and -2, JAQ1, mAB 10B12, mAB 1C3, mAb 12G1.

In a particular embodiment the compound inhibiting the platelet GPVI receptor is administered together with a prostacyclin or a prostacyclin analog, see below.

9. Compounds inhibiting the PAR receptors such as thrombin inhibitors, heterocycle-based peptide-miimetic antagonists of PAR-1, RWJ-56110 and RWJ-58259, SCH 79797, SCH 203099, and PAR4 antagonists such as trans-cinnamoyl-YPGKF-amide (tc-Y-NH(2)) and palmitoyl-SGRRYGHALR-amide (P4pa110), PAR-2 antagonist ENMD-1068, PAR2 monoclonal antibody SAM-11.

In a particular embodiment the compound inhibiting the PAR receptors is administered together with a prostacyclin or a prostacyclin analog, see below.

10. Phosphodiesterase inhibitor PDE3 such as Cilostazol with therapeutic focus on increasing cAMP. An increase in cAMP results in an increase in protein kinase A (PKA), which is directly related with an inhibition in platelet aggregation.

In a particular embodiment the Phosphodiesterase inhibitor is administered together with a prostacyclin or a prostacyclin analog, see below.

11. Nitroaspirin (NCX4016) an aspirin that can release NO.

In a particular embodiment nitroaspirin is administered together with a prostacyclin or a prostacyclin analog, see below 12. A compound of albumin conjugated with polyethylene glycol (PEG).

In a particular embodiment the albumin conjugated with PEG inhibitor is administered together with a prostacyclin or a prostacyclin analog, see below.

13. A compound of haemoglobin conjugated with polyethylene glycol, a compound that besides its platelet inhibitory function also improves oxygenation of the microvasculature, such as but not exclusively MP40X (Hemospan, polyethylene glycol-hemoglobin complexes)

In a particular embodiment the hemoglobin conjugated to PEG is administered together with a prostacyclin or a prostacyclin analog, see below.

14. Antibodies and/or inhibitors of C-type lectin-like receptor 2 (CLEC-2) [May et al 2009] In a particular embodiment the antibodies/inhibitors of CLEC-2 is administered together with a prostacyclin or a prostacyclin analog, see below.

15. High-energy glycolitic metabolites like fructose-1,6-bisphosphate (FBP) [de Oliveira et al]

In a particular embodiment the FBP is administered together with a prostacyclin or a prostacyclin analog, see below.

In a preferred embodiment the platelet inhibitor has a half time of less than 3 hours (such as eptifibatide), preferably less than 2.5 hours (such as tirofiban), more preferably less than 1 hour (such as abciximab). In a preferred embodiment a compound inhibiting the platelet GPIIb/IIIa receptor is administered. Eptifibatide is an example of a most preferred compound.

In another preferred embodiment the platelet inhibitor has a half time of less than 12 hours (such as Ticlopidine), preferably less than 8 hours (such as Clopidogrel), more preferably about 3-5 min (such as cangrelor). Another preference is in the reversibility of the ADP receptor inhibition: Ticagrelor is an example of a compound that blocks the receptor in a reversible manner and Ticagrelor is for this reason preferable. Thus in an equally preferred embodiment a compound inhibiting the platelet ADP receptor (P2Y12) is administered.

In regards to the half lives/half times of the herein mentioned compounds: the half time depends on the administration form and/or the dosage. In general, intravenous administration is preferred.

Agents Modulating/Preserving Endothelial Integrity

The endothelium maintains under physiological conditions a normal vascular function by regulating the balance between vasodilator and vasoconstrictor mediators and by regulating the expression of adhesion receptors. Endothelial modulators encompass any agent that affects the endothelium to either maintain or develop into a non-activated quiescent state, which optimally preserves and ensures vascular integrity. In a state with vascular integrity, the endothelium exerts anti-inflammatory and anti-thrombotic properties down-regulating and counteracting platelet activation through the generation of PGI2 (prostaglandin 12, prostacyclin) and through the production of ADPase, the latter catalyzing the degradation of ADP. Endothelial cells can also prevent the activation of the coagulation cascade by expressing surface molecules with anticoagulant properties such as heparan sulfate, dermatan sulfate, tissue factor pathway inhibitor (TFPI), protein S (PS) and thrombomodulin (TM). Endothelial cells express plasminogen, tissue-type plasminogen activator (tPA), urokinase-type plasminogen activator (uPA), urokinase-type plasminogen activator receptor (uPAR) as well as membrane-associated plasminogen activator binding sites, thus favouring the generation of plasmin, and they express endothelial protein C receptor (EPCR), which enhances the anticoagulant activity.

The endothelial modulators may be selected from any of the classes of compounds (1-11) described below:

1. Compounds such as PGI2, PGX, prostacyclin (Epoprostenol) or variants thereof, such as beraprost sodium, epoprostenol sodium, iloprost, iloprost in combination with bosentan, iloprost in combination with sildenafil citrate, treprostinil, pegylated treprostinil, treprostinil diethanolamine and treprostinil sodium. Further compounds are 2-{4-[(5,6-diphenylpyrazin-2-yl)(isopropyl) amino]butoxy}-N-(methylsulfony-1)acetamide, {4-[(5, 6-diphenylpyrazin-2-yl)(isopropyl)amino] butoxy}acetic acid, 8-[1,4,5-triphenyl-1H-imidazol-2-yl-oxy]octanoic acid, isocarbacyclin, cicaprost, [4-[2-(1,1-Diphenylethylsulfanyl)-ethyl]-3,4-dihydro-2H-benzo[1,4]oxazin-8-yloxy]-acetic acid N-Methyl-d-glucamine, 7,8-dihydro-5-(2-(1-phenyl-1-pyrid-3-yl-methiminoxy)-ethyl)-α-naphthyloxy-acetic acid, (5-(2-diphenylmethyl aminocarboxy)-ethyl)-a-naphthyloxyaceticacid, 2-[3-[2-(4,5-diphenyl-2-oxazolyl)ethyl]phenoxy]acetic acid, [3-[4-(4,5-diphenyl-2-oxazolyl)-5-oxazolyl]phenoxy]acetic acid, bosentan, 17[alpha],20-dimethyl-[DELTA]6,6a-6a-carba PGI1, and 15-deoxy-16 [alpha]-hydro xy-16 [beta],20-dimethyl-[DELTA]6,6a-6a-carba PGI1, pentoxifylline(1-{5-oxohexyl}-3,7-dimethylxanthine).

Trade names for prostacyclins include, but are not limited to: flolan, remodulin, and ventavis.

2. A combination of prostacyclin or a prostacyclin analogue and endothelin receptor antagonist may improve the safety profile of prostacyclin therapy by reducing potential side effects of prostacyclin such as jaw pain, headache and hypotension.

3. Compounds with modulating/preserving endothelial effects such as nitric oxide (also Endothelium Derived Relaxing Factor) produced by healthy endothelial cells induce vasodilatation and favours an anti-adhesive and anti-inflammatory phenotype of the endothelium through a rise in cytosolic cGMP [Cines et al 1998; Zardi et al 2005].

4. CD39 and CD73 are vascular membrane-bound ecto-nucleotidases expressed at the luminal surface of healthy endothelial cells. They hydrolyze extracellular plasma ATP and ADP and thereby inhibit nucleotide mediated platelet activation [Atkinson et al 2006; Colgan et al 2006]. In addition to platelet inhibition, soluble CD39 and CD73 agonists inhibit endothelial cell apoptosis and activation [Goepfert et al 2000] and prevent hypoxia induced vascular leakage [Thompson et al 2004].

5. Compounds involved in redox control of endothelial functions such as: L-Arginine and tetrahydrobiopterin, Antioxidants (Ascorbate, Glutathione, α-tocopherol, ubiquinol-10, Probucol), Iron chelators, and Polyphenols.

6. Clinical drugs involved in redox control of endothelial functions such as: HMG-CoA reductase inhibitors (Fluvastatin, Lovastatin, Pravastatin, Simvastatin), Angiotensin-receptor antagonists and ACE inhibitors (Captopril, Zofenopril, Enalapril, Ramipril, Quinapril, Perindopril, Lisinopril, Benazepril, Fosinopril, Casokinins, lactokinins), Peroxisome proliferator-activated receptors (PPARs), NADPH oxidase, Xanthine oxidase, PETN, Heparan sulfates (PI-88), heparan sulfate mimetics, Activators of oxidized/heme-free sGC (BAY 58-2667), and Anti-PECAM/SOD.

7. Honokiol, a biphenyl neolignan isolated from Hou pu, the cortex of *Magnolia officinalis*.

8. Compounds that directly modulate endothelial barrier function through modulating effects on sphingosine-1-phosphate (S1P)-receptors (eg.: FTY720, AA-R, AAL-S, KRP-203, AUY954, CYM-5442, SEW2871, W146, W140, VPC44116, VPC23019, JTE-013) [Marsolais et al 2009].
9. Antibodies and/or other molecules against/antagonizing histones that through their inhibition diminishes histone-mediated endothelial damage and/or microthrombi formation and/or fibrin deposition [Xu et al 2009].
10. Compounds enhancing the natural anticoagulant pathways and hence protecting the endothelium such as but not exclusively: Protein C pathway (Activated protein C (APC, Drotrecogin alfa), protein C, compounds that either mimics and/or protects from degradation and/or enhances soluble thrombomodulin and/or EPCR and/or protein S), Antithrombin III (ATIII) (or ATIII like compounds and/or compounds that enhance ATIII function) and tissue factor pathway inhibitor (TFPI) (or TFPI compounds and/or compounds that enhance TFPI function).
11. Compounds that maintain and/or promote Gβγ function and/or signalling following endothelial PAR activation to ensure reannealing of adherens junctions opened following inflammatory PAR mediated activation of Gα[Knezevic et al 2009]

Various other potential target sites to modulate the endothelial function, activation state and integrity are given in Table 3, below.

TABLE 3

Potential endothelial modulating target sites

| Targets | Compound |
|---|---|
| 1. Inhibition of Rho-kinase | Fasudil |
| | Y-27632 |
| 2. Inhibition of PARP | PJ-34 |
| | INO 1001 |
| | 3-Aminobenzamide |
| 3. Inhibition of PTPase | Bis(malotalo) oxovanadium |
| 4. Activation of Akt | Demethylasterriquinone |
| 5. Activation of PKA | 8-Br-cAMP |
| 6. Inhibition of caveolin | Daidzein |
| 7. estrogen-receptor (ER) agonist | 17-beta-Estradiol |
| 8. Activation of | |
| PPAR alpha | Fibrates |
| PPAR gamma | Thiazolidinediones |
| PPAR delta | GW 07242 |
| 9. Inhibition of CETP | Torcetrapib |
| | CETi-1 vaccine |
| 10. Activation of lipoprotein lipase | NO-1886 |
| 11. Activation of S1P | FTY720 |
| 12. Activation of transketolase | Benfotiamine |
| 13. Inhibition of GGT | GGTI-298 |
| 14. Inhibition of epoxide hydrolase | 1-Cyclohexyl-3-dodecylurea |
| | N,N'-Dicyclohexylurea |
| | N,N'-Adamantanyl-N'-dodecanoic urea |
| 15. Activation of ACE 2 | AVE 0991 |
| 16. Inhibition of JAK | AG-490 |
| | WHI-P154 |

Prostacyclin, a metabolite of arachidonic acid, is a naturally occurring prostaglandin with potent vasodilatory activity and inhibitory activity of platelet aggregation, released by healthy endothelial cells. Prostacyclin performs its function through a paracrine signalling cascade that involves G protein-coupled receptors on nearby platelets and endothelial cells. In the clinical setting, Epoprostenol (prostacyclin analogue) has 2 major pharmacological actions: (1) direct vasodilation of pulmonary and systemic arterial vascular beds, and (2) inhibition of platelet aggregation. Epoprostenol is indicated for the long-term intravenous treatment of primary pulmonary hypertension and pulmonary hypertension associated with the scleroderma spectrum of disease in NYHA Class III and Class IV patients who do not respond adequately to conventional therapy. The antiaggregatory effect of prostacyclin analogs on platelets is mediated by the Gas protein-coupled receptor (prostacyclin receptor, IP) that is activated upon prostacyclin analog binding. This activation signals adenylyl cyclase to produce cAMP, which in turn activates Protein Kinase A to decrease free intracellular calcium concentrations. The rise in cAMP directly inhibits platelet activation (secretion and aggregation) and counteracts increases in cytosolic calcium resulting from platelet activation by agonists such as thrombin, ADP, TXA2, PAF, collagen and 5-HT [Bihari et al, 1988; Schereen et al, 1997; Xing et al 2008].

The modulating/preserving effect on endothelial integrity is mediated by binding of prostacyclin analog to endothelial prostacyclin receptors with ultimate rise in cytosolic cAMP and Protein Kinase A activation. This leads to smooth muscle relaxation and vasodilatation with improved microvascular perfusion and "cytoprotection" through stabilization of lysozomal and cell membranes with reduced inflammation. It also favours an anti-coagulant, anti-adhesive, anti-apoptotic and anti-inflammatory phenotype of the endothelium, less likely to support coagulation, leukocyte adhesion/migration and inflammation [Zardi et al 2005; Zardi et al 2007].

In a preferred embodiment the compound capable of modulating/preserving the endothelial integrity has a half time of less than 4 hours (such as Treprostinil), preferably less than 1 hours (such as Beraprost (35-40 min)), more preferably less than ½ hour (such as Iloprost (20-30 min)), preferably less than 5 min (such as Epoprostenol (0.5-3 min))

Pro-fibrinolytics

Also denoted compounds capable of augmenting the fibrinolytic activity in whole blood. This group includes compounds such as (t-PA, u-PA) or (rt-PA, ru-PA) such as: Actilyse, Metalyse, Rapilysin, Streptase, Urokinase and other compounds containing t-PA and/or rt-PA, uPA, r-uPA.

TAFIa Inhibitors

Also denoted compounds that inhibit thrombin-activatable fibrinolysis inhibitor (TAFIa). Compounds included in this class are for example CPU-I, AZD9684, MERGETPA, Compound 21 (UK-396,082) and other compounds with a similar effect.

Combinations

Administration of combinations of the compounds discussed herein is also envisaged by the present invention as discussed above.

The invention relates to a pharmaceutical composition comprising one or more one or more compounds selected from the group consisting of platelet inhibitors, compounds capable of modulating/preserving the endothelial integrity, compounds capable of augmenting the fibrinolytic activity, or TAFIa inhibitors.

Thus the invention relates to any combination of any of the classes of compounds mentioned above (platelet inhibitors, endothelial modulators, pro-fibrinolytics, TAFIa-inhibitors), such as one compound, such as at least two compounds, such as at least three compounds. When using more than one compound the compounds may be selected from the same class of compounds, or more preferably the at least two compounds may be selected from different classes of compounds.

Accordingly, in one embodiment one compound is selected from a compound capable of modulating/preserving the endothelium (endothelial modulator) and the at least one other compound is selected from a compound capable of inhibiting the platelets (platelet inhibitor), a compound capable of increasing fibrinolysis either directly (pro-fibrinolytics) or indirectly (TAFIa-inhibitors).

In another embodiment one compound is selected from a compound capable of inhibiting the platelets (platelet inhibitor) and the at least one other compound is selected from a compound capable of modulating/preserving the endothelium or increasing fibrinolysis directly (pro-fibrinolytics) or indirectly (TAFIa-inhibitors).

In a third embodiment one compound is selected from a compound capable of directly enhancing fibrinolysis (pro-fibrinolytics) and the at least one other compound is a TAFIa-inhibitor.

Accordingly, combination treatment may include administration of any combination of one or more anti-thrombotic compounds, such as one or more of the following: platelet inhibitors including but not limited to GPIIb/IIIa inhibitors, ADP receptor inhibitors, P2Y1 inhibitors, COX1 and COX2 inhibitors, TX-synthase inhibitors, adenosine uptake inhibitors, GPIb inhibitors, GPVI inhibitors, PAR receptor inhibitors, phosphodiesterase inhibitors, nitroaspirin, albumin conjugated with polyethylene glycol, MP4OX, anti-CLEC-2 antibodies, FBP or similar compounds and/or endothelial modulators including but not limited to PGI2/prostacyclin analogues and variants hereof, prostacyclin/prostacyclin analogue combined with endothelin receptor antagonists, NO, CD39, CD73, compounds involved in redox control, clinical drugs involved in redox control (HMG-CoA reductase inhibitors), Honokiol, compounds modulating S1P-receptors, antibodies and/or other molecules against/antagonizing histones, compounds enhancing/modulating the natural anticoagulant pathways such as the protein C pathway including but not limited to APC, PC, PS, sTM, sEPCR), ATIII pathway (ATIII), TFPI pathway (TFPI), Gβγ stimulators and/or any pro-fibrinolytics such as t-PA, u-PA, rt-PA, ru-PA (Actilyse, Metalyse, Rapilysin, Streptase, Urokinase and other compounds containing t-PA and/or rt-PA, uPA, r-uPA and any TAFIa-inhibitors including but not limited to CPU-I, AZD9684, MERGETPA, Compound 21 (UK-396,082) and other compounds with a similar effect.

Thus, in preferred embodiments platelet inhibitor is selected from the group consisting of abciximab, eptifibatide, tirofiban, orbofiban, xemilofiban, lamifiban, XJ757, DUP728 and XR299 and the compound capable of modulating/preserving the endothelial integrity is selected from the group consisting of PGI2, PGX, nitrogen oxide, CD39, CD73 and prostacyclin or variants thereof, such as beraprost sodium, epoprostenol sodium, iloprost, iloprost in combination with bosentan, iloprost in combination with sildenafil citrate, treprostinil, pegylated treprostinil, treprostinil diethanolamine and treprostinil sodium, 2-{4-[(5,6-diphenylpyrazin-2-yl)(isopropyl)amino]butoxy}-N-(methylsulfony-1)acetamide, {4-[(5,6-diphenylpyrazin-2-yl)(isopropyl)amino]butoxy}acetic acid, 8-[1,4,5-triphenyl-1H-imidazol-2-yloxy]octanoic acid, isocarbacyclin, cicaprost, [4-[2-(1,1-Diphenylethylsulfanyl)-ethyl]-3,4-dihydro-2H-benzo[1,4]oxazin-8-yloxy]-acetic acid N-Methyl-d-glucamine, 7,8-dihydro-5-(2-(1-phenyl-1-pyrid-3-yl-methiminoxy)-ethyl)-a-naphthyloxy-acetic acid, (5-(2-diphenylmethyl aminocarboxy)-ethyl)-a-naphthyloxyaceticacid, 2-[3-[2-(4,5-diphenyl-2-oxazolyl]ethyl]phenoxy]acetic acid, [3-[4-(4,5-diphenyl-2-oxazolyl)-5-oxazolyl]phenoxy]acetic acid, bosentan, 17 [alpha],20-dimethyl-[DELTA]6,6a-6a-carba PGI1, 15-deoxy-16 [alpha]-hydroxy-16 [beta],20-dimethyl-[DELTA]6,6a-6a-carba PGI1 and pentoxifylline(1-{5-oxohexyl}-3,7-dimethylxanthine).

In another equally preferred embodiment the platelet inhibitor is selected from the group consisting of AR-C69931 MX, Ticlopidine, Clopidogrel, Prasugrel, AZD6140 and cangrelor, ticagrelor and the compound capable of modulating/preserving the endothelial integrity is selected from the group consisting of PGI2, PGX, nitrogen oxide, CD39, CD73 and prostacyclin or variants thereof, such as beraprost sodium, epoprostenol sodium, iloprost, iloprost in combination with bosentan, iloprost in combination with sildenafil citrate, treprostinil, pegylated treprostinil, treprostinil diethanolamine and treprostinil sodium, 2-{4-[(5,6-diphenylpyrazin-2-yl)(isopropyl)amino]butoxy}-N-(methylsulfony-1)acetamide, {4-[(5,6-diphenylpyrazin-2-yl)(isopropyl)amino]butoxy}acetic acid, 8-[1,4,5-triphenyl-1H-imidazol-2-yloxy]octanoic acid, isocarbacyclin, cicaprost, [4-[2-(1,1-Diphenylethylsulfanyl)-ethyl]-3,4-dihydro-2H-benzo[1,4]oxazin-8-yloxy]-acetic acid N-Methyl-d-glucamine, 7,8-dihydro-5-(2-(1-phenyl-1-pyrid-3-yl-methiminoxy)-ethyl)-a-naphthyloxy-acetic acid, (5-(2-diphenylmethyl aminocarboxy)-ethyl)-a-naphthyloxyacetic acid, 2-[3-[2-(4,5-diphenyl-2-oxazolyl)ethyl]phenoxy]acetic acid, [3-[4-(4,5-diphenyl-2-oxazolyl)-5-oxazolyl]phenoxy]acetic acid, bosentan, 17 [alpha],20-dimethyl-[DELTA]6,6a-6a-carba PGI1, 15-deoxy-16 [alpha]-hydroxy-16 [beta],20-dimethyl4DELTA]6,6a-6a-carba PGI1 and pentoxifylline(1-{5-oxohexyl}-3,7-dimethylxanthine).

In other preferred embodiments the platelet inhibitor is capable of inhibiting the GPIIb/IIIa receptor and has a half time of less than 3 hours (such as eptifibatide), preferably less than 2.5 hours (such as tirofiban), more preferably less than 1 hour (such as abciximab) and the compound capable of modulating/preserving the endothelial integrity a half time of less than has a half time of less than 4 hours (such as Treprostinil), preferably less than 1 hours (such as Beraprost (35-40 min)), more preferably less than ½ hour (such as Iloprost (20-30 min)), preferably less than 5 min (such as Epoprostenol (0.5-3 min)).

In other preferred embodiments the platelet inhibitor is capable of inhibiting platelet ADP receptor P2Y12 and has a half time of 12 hours (such as Ticlopidine), preferably less than 8 hours (such as Clopidogrel), more preferably about 3-5 min (such as cangrelor) and the compound capable of modulating/preserving the endothelial integrity a half time of less than has a half time of less than 4 hours (such as Treprostinil), preferably less than 1 hours (such as Beraprost (35-40 min)), more preferably less than ½ hour (such as Iloprost (20-30 min)), preferably less than 5 min (such as Epoprostenol (0.5-3 min))

Furthermore, the treatment may include administration of one or more of the antithrombotic compounds mentioned above in combination with therapies including but not limited to plasma exchange or plasma infusion, and/or anticoagulation with heparins (such as UFH, LMWH), and/or antithrombin and/or activated protein C and/or TFPI and/or coumadins and/or direct or indirect thrombin inhibitors and/or direct or indirect factor Xa inhibitors.

In particular a combination of platelet inhibitors and compound capable of modulating/preserving endothelial integrity is envisaged by the present invention, such as a combination of a GPIIb/IIIa platelet inhibitor and a prostacyclin, optionally further combined with other compounds. A preferred combination is GPIIb/IIIa platelet inhibitor and a prostacyclin further combined with endothelin receptor antagonists.

Furthermore, the term "treatment" also includes administration of a fibrinolysis activator, such as tissue plasminogen activator (tPA), urokinase plasminogen activator (uPA) or variants hereof alone or in any combination of therapies including but not limited to antithrombotics and/or endothelial modulators (such as prostacyclin, NO) and/or plasma exchange, plasma infusion, and/or anticoagulation with heparins (such as UFH, LMWH), and/or antithrombin and/or activated protein C and/or TFPI and/or coumadins and/or direct or indirect thrombin inhibitors and/or direct or indirect factor Xa inhibitors).

The compounds to be applied in the method of the present invention may be administered with at least one other compound. The compounds may be administered simultaneously, either as separate formulations or combined in a unit dosage form, or administered sequentially.

Dosages

As used herein, "dose" shall mean any concentration of the agents administered to the patient resulting in inhibition of the aggregating/clot forming properties of the platelets and/or maintaining the endothelium in a quiescent state and/or a reduced resistance of the thrombus to fibrinolysis and/or preserving the platelet count and/or function. A dose sufficient to produce the desired effect in relation to the conditions for which it is administered shall be described as the "effective dose" or "effective amount".

As will be understood by the person skilled in the art, amounts effective for this purpose will depend on the number and functionality of circulating platelets and endothelial cells in the patient and the number of receptors on the respective platelets and endothelial cells.

The dosage requirements will vary with the particular drug composition employed, the route of administration and the particular subject being treated. Ideally, a patient to be treated by the present method will receive a pharmaceutically effective amount of the compound in the maximum tolerated dose, generally no higher than that required before drug resistance develops.

Administration of the compounds and/or compositions of the present invention are to be given to a subject resulting in a systemic concentration of the compounds. Methods of administration include enteral, such as oral, sublingual, gastric or rectal and/or parenterally, that is by intravenous, intraarterial, intramuscular, subcutaneous, intranasal, intrapulmonary, intrarectal, intravaginal or intraperitoneal administration. The subcutaneous and intravenous forms of parenteral administration are generally preferred. Appropriate dosage forms for such administration may be prepared by conventional techniques. The compounds may also be administered by inhalation that is by intranasal and oral inhalation administration. Appropriate dosage forms for such administration, such as an aerosol formulation or a metered dose inhaler, may be prepared by conventional techniques.

The compounds according to the invention may be administered with at least one other compound. The compounds may be administered simultaneously, either as separate formulations or combined in a unit dosage form, or administered sequentially.

Normally the dose should be capable of preventing or lessening the severity or spread of the condition or indication being treated. The exact dose will depend on the circumstances, such as the condition being treated, the administration schedule, whether the compounds are administered alone or in conjunction with another therapeutic agent, the plasma half-life of the compounds and the general health of the subject.

The compounds disclosed herein are generally well known to a person skilled in the art and the appropriate dosages for their use are disclosed in pharmacopeias, pharmaceutical handbooks, and patient information leaflets. Thus the compounds of the present invention may be administered n the dosages recommended by the manufacturers or as are known to be efficient to those skilled in the art, i.e. medical practitioners.

As will be understood by the person skilled in the art, amounts effective for this purpose will depend on the severity of the disease or injury as well as the weight and general state of the subject. The dose is preferably given by the parenteral administration route, notably the intravenous, intraarterial, intramuscular and/or the subcutaneous, sublingual, trans-mucosal, intrapulmonal and intra-alveolar route.

The dosages given in the following is contemplated to be in the same order of magnitude irrespective of the parenteral administration route.

For all methods of use disclosed herein for the compounds, the daily parenteral dosage regimen about 0.001 to about 80 mg/kg of total body weight. The daily oral dosage regimen will preferably be from about 0.01 to about 80 mg/kg of total body weight. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound or a pharmaceutically acceptable salt thereof given per day for a defined number of days, can be ascertained by those skilled in the art using conventional course of treatment determination tests.

The term "unit dosage form" as used herein refers to physically discrete units suitable as unitary dosages for human and animal subjects, each unit containing a predetermined quantity of a compound, alone or in combination with other agents, calculated in an amount sufficient to produce the desired effect in association with a pharmaceutically acceptable diluent, carrier, or vehicle. The specifications for the unit dosage forms of the present invention depend on the particular compound or compounds employed and the effect to be achieved, as well as the pharmacodynamics associated with each compound in the host It is an object of the present invention that the compounds and/or compositions herein disclosed are administered systemically. It is also an object of the present invention that the compounds are administered parenterally, preferably intravenously and/or intrarterially.

Pharmaceutical Compositions of the Invention and its Use

The present invention also relates to a pharmaceutical composition comprising any combination of any of the compounds mentioned above (platelet inhibitors, endothelial modulators, pro-fibrinolytics, TAFIa-inhibitors), such as one compound, such as at least two compounds, such as at least three compounds and one or more pharmaceutically acceptable carriers or excipients. Such pharmaceutically acceptable carrier or excipient as well as suitable pharmaceutical formulation methods are well known in the art (see for example Remington's Pharmaceutical Sciences, 18th ed., Mack Publishing Company, Easton, Pa. (1990). In a preferred embodiment the platelet inhibiting/endothelial protecting variants are prepared in a parenteral composition. Such methods for preparing parenterally administrable compositions will also be known or apparent to those skilled in the art and are described in more detail in, for example, Remington's Pharmaceutical Sciences, 18th ed., Mack Publishing Company, Easton, Pa. (1990). As used herein, the term "pharmaceutical acceptable" means carriers or excipients that does not cause any untoward effects in subjects to whom it is administered.

The compositions for parenteral administration comprise the platelet antiaggregatory agents of the invention in combination with, preferably dissolved in, a pharmaceutically acceptable carrier, preferably an aqueous carrier. A variety of aqueous carriers may be used, such as water, buffered water, saline e.g. such as 0.7%, 0.8%, 0.9% or 1%, glycine such as 0.2%, 0.3%, 0.4% or 0.5% and the like. Normally, it is aimed that the composition has an osmotic pressure corresponding to a 0.9% w/w sodium chloride solution in water. Moreover, as known by a person skilled in the art, dependent on the specific administration route, pH may be adjusted within suitable ranges centred around pH 7.4. The compositions may be sterilised by conventional, well-known sterilisation techniques. The resulting aqueous solutions may be packaged for use or filtered under aseptic conditions and lyophilised, the lyophilised preparation being combined with a sterile aqueous solution prior to administration.

The compositions may contain pharmaceutically acceptable auxiliary substances as required to approximate physiological conditions, such as pH adjusting and buffering agents, stabilizing agents, preservatives, non-ionic surfactants or detergents, antioxidants, tonicity adjusting agents and the like, for example, sodium acetate, sodium lactate, sodium chloride, potassium chloride, calcium chloride, etc.

The main routes of drug delivery, in the treatment method are intravenous, oral, and topical, as will be described below. Other drug-administration methods, such as subcutaneous injection or via inhalation, which are effective to deliver the drug to a target site or to introduce the drug into the bloodstream, are also contemplated.

Compounds of the invention may be administered parenterally, that is by intravenous, intramuscular, subcutaneous intranasal, intrarectal, intravaginal or intraperitoneal administration. Appropriate dosage forms for such administration may be prepared by conventional techniques. The compounds may also be administered by inhalation that is by intranasal and oral inhalation administration. Appropriate dosage forms for such administration, such as an aerosol formulation or a metered dose inhaler, may be prepared by conventional techniques.

The compounds are preferably administered intravenously and/or intraalveolar and it may be administered by continuous or pulsatile infusion or as a bolus.

The compounds to be applied in the method of the present invention may be administered with at least one other compound. The compounds may be administered simultaneously, either as separate formulations or combined in a unit dosage form, or administered sequentially. It is thus also contemplated that one compound may be administered intravenously for example in combination with another compound that is administered orally.

Clinical Indications

As described herein above the present invention relates to treatment and/or prevention of organ failure, wherein organ failure is defined as altered organ function in a critically ill patient requiring medical intervention to achieve homeostasis. Organ failure includes as used herein MOF and TAMOF, in at least one organ, such as in at least two, three, four or five organs.

Furthermore, the compounds and/or pharmaceutical compositions described herein are also suitable for prophylaxis, reduction and/or treatment of any conditions and/or diseases associated with systemic inflammation (low-grade as well as high-grade) and/or enhanced platelet and/or endothelial activation and/or dysregulation are suitable for prophylaxis and/or treatment with compounds of the invention.

TABLE 4

Non-exclusive list of conditions associated with systemic inflammation, according to pathology, suitable for prophylaxis and/or treatment by compounds of the invention.

| Condition | Pathology |
| --- | --- |
| Infections | Any microorganism (bacteria (intra-, extracellular, myco-), virus, fungi, parasites, prions) |
| Non-infectious antigens | Organ/stem cell transplantation, blood transfusion, biological drugs |
| Trauma | Blunt, penetrating trauma, polytrauma, neurotrauma, minor, major |
| Burns/freeze burns | |
| Organ/tissue destruction/degeneration/ damage | Pancreatitis Irradiation |
| Ischemia | Atherosclerosis, thrombi, emboli (cholesterol, fat, air, septic, tissue, foreign body, amniotic fluid), trauma, vascular occlusion, vasculitis, aneurysms, severe anemia |
| Haemorrhage | |
| Intoxication | Alcohol, recreational drugs, iatrogenic (chemotherapy, overdose, interaction, adverse event), snake/insect bites |
| Malignancy | Myeloproliferative/lymphoproliferative malignancies, solid tumors metastasis |

TABLE 5

Non-exclusive list of conditions and/or diseases associated with systemic inflammation, according to medical speciality and/or anatomical localization, suitable for prophylaxis and/or treatment by compounds of the invention.

| Conditions and/or diseases associated with systemic inflammation | Medical speciality and/or anatomical localization |
| --- | --- |
| The following manifestations whatever their cause | SIRS, compensatory anti-inflammatory response syndrome (CARS), shock, organ failure, MOF, DIC, coagulopathy Microthrombi/emboli/occlusion (imminent, suspected, manifest) in one or more organs |
| Severe infections caused by any microorganism including | Sepsis, severe sepsis, septic shock, organ failure, MOF, DIC Necrotisizing fasciitis |
| Surgery, trauma and/or burns including | SIRS, compensatory anti-inflammatory response syndrome, Shock, tissue hypoperfusion, base deficit, lactate acidosis, MOF, DIC, coagulopathy (hypercoagulability, hypocoagulability, hyperfibrinolysis) |

TABLE 5-continued

Non-exclusive list of conditions and/or diseases associated with systemic inflammation, according to medical speciality and/or anatomical localization, suitable for prophylaxis and/or treatment by compounds of the invention.

| Conditions and/or diseases associated with systemic inflammation | Medical speciality and/or anatomical localization |
|---|---|
| Malignant diseases and chemotherapeutic/immunosuppressive treatment | Solid tumours, haematological malignancies, metastatic tumours Chemotherapy (Alkylating agents (L01A) examplified by Cisplatin, carboplatin and oxaloplatin; Anti-metabolites (L01B) masquerade as purine ((azathioprine, mercaptopurine)) or pyrimidine; Plant alkaloids and terpenoids (L01C) as examplified by Vincristine, Vinblastine, Vinorelbine, Vindesine, Podophyllotoxin. Taxanes (L01CD), Taxol, Docetaxel. Topoisomerase inhibitors (L01CB and L01XX) topotecan, irinotecan, amsacrine, etoposide, etoposide phosphate, teniposide. Antitumour antibiotics (L01D) dactinomycin, doxorubicin, epirubicin, bleomycin. Monoclonal antibodies such as trastuzumab, cetuximab, rituximab, Bevacizumab Irradiation and/or irradiation therapy (Conventional external beam radiotherapy, Virtual simulation, 3-dimensional conformal radiotherapy, and intensity- modulated radiotherapy, Radioisotope Therapy (RIT)) |
| Transplantation and their complications | Solid organs (heart, lungs, liver, kidneys, pancreas, intestines or any combination hereof), allogenic or autologous haematopoietic stem cells, bone marrow, T-cells, B-cells Graft versus host disease (acute, chronic), graft rejection (host vs. graft) |
| Extracorporeal circulation, vascular prosthesis and/or apheresis treatment | Cardiopulmonary bypass, ECMO, ventricular assist devices, non-biologic valvular prosthesis, vascular prosthesis (biological, non-biological) in any location in the human organism Plasmapheresis, leukapheresis, dialysis, renal replacement therapy |
| Toxins | Spider, snake, scorpion, jellyfish, wasp, bee, poison dart frog, honeybee, Cyanotoxins, Pit vipers, such as rattlesnakes |
| Neurological diseases | Degenerative diseases (Parkinson's disease, Alzheimer's disease), Stroke, Neurotrauma (brain, spinal cord), Seizure disorders (epilepsy), Malignancies (brain/spinal cord tumors), Infections (meningitis, encephalitis) |
| Cardiovascular diseases | Angina, Atherosclerosis, Cardiomyopathy, Congestive heart failure, Coronary artery disease, Carotid artery disease, Endocarditis, Heart attack (coronary thrombosis, myocardial infarction), Hypertension, Hypercholesterolemia/hyperlipidemia, Peripheral artery disease, Stroke |
| Respiratory diseases | Asthma, Bronchitis, Emphysema, Chronic obstructive pulmonary disease, Infections (exemplified by influenza, pneumonia and tuberculosis), Malignancies (Lung cancer), Sarcoidosis, Pleurisy |
| Gastrointestinal diseases | Inflammatory bowel diseases (Colitis ulcerosa, Mb Crohn's disease) |
| Hepatic diseases | Alcoholic liver disease, Cholangiocarcinoma, Hepatitis, Hepatic encephalopathy, Hepatic failure, Liver abscess, Malignant/benign liver tumours, Liver cirrhosis, Liver coagulopathy, Glycogen storage diseases, Portal hypertension, Primary biliary cirrhosis, Primary sclerosing cholangitis |
| Renal diseases | Acute/chronic kidney failure, Acute nephritic syndrome, Atheroembolic renal disease, Chronic nephritis, Nephrotic syndrome, End-stage renal disease, Goodpasture syndrome, Interstitial nephritis, Kidney cancer/damage/infection/injury/stones, Lupus nephritis, Glomerulonephritis, Membranous nephropathy, Nephroblastoma, |

TABLE 5-continued

Non-exclusive list of conditions and/or diseases associated with systemic inflammation, according to medical speciality and/or anatomical localization, suitable for prophylaxis and/or treatment by compounds of the invention.

| Conditions and/or diseases associated with systemic inflammation | Medical speciality and/or anatomical localization |
|---|---|
| Endocrine diseases | Nephrocalcinosis, Nephrogenic diabetes insipidus, Nephropathy - IgA, Polycystic kidney disease, Reflux nephropathy, Renal papillary necrosis, Renal tubular acidosis Adrenal disorders (Adrenal insufficiency, Addison's disease, Mineralocorticoid deficiency, Conn's syndrome, Cushing's syndrome, Pheochromocytoma, Adrenocortical carcinoma) Glucose homeostasis disorders (Diabetes mellitus, Hypoglycemia, Idiopathic hypoglycemia, Insulinoma) Metabolic bone disease Pituitary gland disorders (Diabetes insipidus, Hypopituitarism (or Panhypopituitarism), Pituitary tumors, Hyperprolactinemia, Acromegaly, gigantism, Cushing's disease Parathyroid gland disorders (Primary/Secondary/Tertiary hyperparathyroidism, Hypoparathyroidism, Pseudohypoparathyroidism) Menstrual function or fertility disorders (Polycystic ovary syndrome) Thyroid disorders (Goiter, Hyperthyroidism and Graves- Basedow disease, Hypothyroidism, Thyroiditis, Thyroid cancer, Tumours of the endocrine glands, Multiple endocrine neoplasia, Autoimmune polyendocrine syndromes) |
| Gynaecologic/obstetric diseases | Obstetric complications (Preeclampsia, eclampsia, HELLP syndrome, amniotic fluid embolism, abruptio placentae) |
| Orthopedic diseases | Trauma, Surgery, Fractures, Malignancies of bone, cartilage and soft tissues including Multiple Myeloma, Arthritis (Osteoarthritis, Rheumatoid arthritis), Cerebral Palsy, Osteonecrosis, Gout, Infections, Myasthenia, Osteoporosis, Pagets disease, Spondylitis |
| Haematological diseases | Malignant (Leukaemia, Myelodysplastic syndrome) Non-malignant (Thrombotic thrombocytopenic purpura, haemolytic- uraemic syndrome, aplastic anaemia, Hemophagocytic Lymphohistiocytosis) |
| Infectious diseases caused by any microorganism exemplified by bacteria (intra-,extracellular, myco-), virus, fungi, parasites, prions) | Infections caused by any microorganism in the cardiovascular, respiratory, renal, haematological, neurological, gastrointestinal, hepatic and musculoskeletal organs, such as heart, vessels, microvasculature, lungs, kidney, bone marrow, brain, gut, pancreas, liver, bones, joints and muscles Endocarditis, Meningitis, Encephalitis, Diarrhea, Hepatitis, Urinary Tract Infections, Intra-Abdominal Infections, Pneumonia, Pharyngitis, Joint Infections, Skin and Soft Tissue infections |
| Allergic diseases | Anaphylaxis, asthma, eosinophil esophagitis, food allergy, urticaria, insect sting allergy, rhinitis, sinusitis, immunodeficiency, mastocytosis |
| Immunologic/rheumatologic diseases | Systemic autoimmune diseases (Rheumatoid arthritis (juvenile and/or adult form), systemic lupus erythro- matosis, sclerodermia, antiphospholipid antibody syndrome, polymyositis, mixed connective tissue disease), Sjogrens syndrome, Fibromyalgia), Sarcoidosis, Vasculitis (Behcet's Disease, Buerger's Disease, Central Nervous System Vasculitis, Churg-Strauss Syndrome, Cryoglobulinemia, Giant Cell Arteritis, Henoch-Schonlein Purpura, Microscopic |

TABLE 5-continued

Non-exclusive list of conditions and/or diseases associated with systemic inflammation, according to medical speciality and/or anatomical localization, suitable for prophylaxis and/or treatment by compounds of the invention.

| Conditions and/or diseases associated with systemic inflammation | Medical speciality and/or anatomical localization |
| --- | --- |
| | Polyangiitis, Polyarteritis Nodosa, Polymyalgia Rheumatica, Rheumatoid Vasculitis, Takayasu's Arteritis, Wegener's Granulomatosis) |
| Inherited disorders | |
| Any identified and/or suspected genetic defects accompanied with disease | |

Accordingly, in one embodiment the present invention relates to a method of treating a critically ill patient, wherein said patient is at increased risk of acquiring organ failure as defined above by administering one or more compounds as discussed above belonging to one or more of the classes:
1. Platelet inhibitors
2. Agents modulating/preserving endothelial integrity
3. Pro-fibrinolytic compounds
4. Inhibitors against TAFIa Optionally combined with further compounds.

The increased risk of organ failure may be judged by the clinical appearance of the patient and/or standard laboratory tests. Furthermore, the critically ill patient may additionally be evaluated by TEG/ROTEM as described herein below as being at risk of acquiring organ failure as discussed above. In particular if the critically ill patient is diagnosed as being hypocoagulable or hypercoagulable, such as when evaluated by TEG/ROTEM, the patient is considered at increased risk of acquiring organ failure.

The patient may be critically ill due to a variety of diseases and conditions, and a non-exhaustive list of clinical conditions associated with systemic inflammation and hence increased risk of organ failure is presented above in Tables 4 and 5.

In one embodiment, the invention thus relates to administration of a compound inhibiting any of the platelet receptors and/or intracellullar pathways mediating platelet activation, alone or in combination with endothelial modulators and/or pro-fibrinolytics and/or TAFIa-inhibitors, as outlined above for the treatment or prophylaxis of systemic inflammation and/or organ failure in patients with any of the disorders described in tables 4 and 5.

In yet another embodiment, the invention thus relates to administration of a compound modulating the vascular endothelium through any of the endothelial receptors and/or intracellullar pathways mediating endothelial activation, alone or in combination with platelet inhibitors and/or pro-fibrinolytics and/or TAFIa-inhibitors, as outlined above for the treatment or prophylaxis of systemic inflammation and/or organ failure in patients with any of the disorders described in tables 4 and 5.

In another embodiment, the invention thus relates to administration of a compound enhancing and/or modulating fibrinolysis through any of the pathways described above, alone or in combination with TAFIa-inhibitors, as outlined above for the treatment or prophylaxis of systemic inflammation and/or organ failure in patients with any of the disorders described in tables 4 and 5.

Thus, one aspect of the invention relates to a pharmaceutical composition comprising one or more of a platelet inhibitor, an endothelial modulator, pro-fibrinolytics and TAFIa-inhibitors either administered alone or in combination of two or three or four compounds for prevention and/or treatment of imminent, suspected or manifest organ failure, wherein organ failure is defined as clinical and/or paraclinical suspected organ dysfunction and/or as altered organ function in an acutely ill patient requiring medical intervention to achieve homeostasis; organ failure includes as used herein MOF and TAMOF in at least one organ, such as in at least two, three, four, five or six organs.

In a particular embodiment the organ failure is due to systemic inflammation or due to severe infections or due to sepsis or due to SIRS and/or CARS or due to coagulopathy or due to trauma and/or burns or due to malignant diseases such as haematological malignancies, solid tumours and metastatic tumours or due to ischemia or due to cardiovascular thromboembolic diseases or due to intoxication.

In a further particular embodiment the organ or organs, which are subject to failure are selected from the group consisting of cardiovascular, respiratory, renal, haematological, neurological, gastrointestinal and hepatic organs and musculoskeletal, such as heart, vessels, microvasculature, lungs, kidney, bone marrow, brain, gut, pancreas, liver, bones, joints and muscles.

Identification of Critically Ill Patients Using TEG

Another aspect of the present invention relates to the identification of critically ill patients using TEG.

Identification of critically ill patients with the highest risk of multiorgan failure (MOF) and treatment of these with interventions that protects the endothelium, prevent pathologic thrombus formation in the microcirculation and preserve platelet number and function may protect these critically ill patients against development of MOF, bleeding and immunodeficiency. Importantly, the notion that the prevention of thrombocytopenia and/or preservation of circulating platelet number and function may be a tool to avoid MOF and immunodeficiency is a shift in the paradigm and based on the emerging role of platelets in the host defence and the inflammatory response where they contribute directly to clear infections and cooperate with and coordinate the function of classical immune cells.

The introduction of the cell based model of haemostasis has emphasized the pivotal role of platelets and the kinetics of thrombin generation for clot development and stability. Together with the finding that the results of the TEG analysis correlate with the individuals ability to generate thrombin an increased interest in this whole blood analysis has revived [Ganter et al. 2008]. The TEG method is described below.

Viscoelastical Citrated Whole Blood Haemostasis Assay: Thrombelastoqraphy (TEG) or Thrombelastometry (ROTEM)

The TEG in vitro assay is suitable for determining important parameters in the clotting activity and clot strength. The TEG system's approach to monitoring patient haemostasis is based on the premise that the end result of the haemostatic process is the clot. The clot's physical properties determine whether the patient will have normal hemostasis, or will be at increased risk for haemorrhage or thrombosis [Salooja et al. 2001].

The TEG analyzer uses a small whole blood sample in a rotating cup and a pin suspended in the blood by a torsion wire, which is monitored for motion. To speed up the clot formation, a standardized amount of an activator of coagulation (e.g. Kaolin, tissue factor) may be added to the cup just before the pin is placed in the cup. The torque of the rotating cup is transmitted to the immersed pin only after fibrin and/or fibrin-platelet bonding has linked the cup and pin together. The strength and rate of these bonds affect the magnitude of the pin motion such that strong clots move the pin directly in phase with cup motion. Thus, the TEG technology documents the interaction of platelets with the protein coagulation cascade from the time of placing the blood in the analyzer until initial fibrin formation, clot rate strengthening and fibrin-platelet bonding via GPIIb/IIIa, through eventual clot lysis. The TEG R parameter reflects the initiation phase, reaction time, from start of coagulation until the first fibrin band is formed; the Angle (a) represents the increase in clot strength, clot kinetics, correlating with the thrombin generation. The maximal amplitude (MA) parameter reflects maximal clot strength i.e. the maximal elastic modus of the clot. Ly30 demonstrate the proportion of the clot that is dissolved 30 min after MA is reached, reflecting fibrinolysis.

The clot strength and stability and changes herein may be measured as increases in relative clot strength by the TEG (Thrombelastography) measurable parameter MA and clot stability by the TEG derivable parameter Lysis AUC. The maximal amplitude (MA) parameter reflects maximal clot strength i.e. the maximal elastic modus of the clot. The area under the lysis curve, i.e. area under the curve from MA is obtained (Lysis AUC) reflects degree of fibrinolysis. Both clot strength and stability may be measured, or one parameter only may be followed during a procedure such as either the clot stability or the clot strength. It is an object of the present invention that the clot strength measured by the MA increases relative to the MA prior to administration of a pro-haemostatic agonist by 105%, such as by 110%, such as by 115%, such as by 120%, such as by 125%, such as by 130%, such as by 135%, such as by 140%, such as by 145%, such as by 150%, such as by 155%, such as by 160%, such as by 165%, such as by 170%, such as by 175%, such as by 180%, such as by 185%, such as by 190%, such as by 195%, such as by 200% or more. Likewise it is an object of the present invention that the clot stability increases Lysis AUC. This parameter may with a TEG analysis be measured e.g. after addition of tissue plasminogen activator (tPA), and thus it is an object of the present invention that the clot stability measured by the Lysis AUC increases relative to the Lysis AUC prior to administration of a sympathicomimetic agonist by 105%, such as by 110%, such as by 115%, such as by 120%, such as by 125%, such as by 130%, such as by 135%, such as by 140%, such as by 145%, such as by 150%, such as by 155%, such as by 160%, such as by 165%, such as by 170%, such as by 175%, such as by 180%, such as by 185%, such as by 190%, such as by 195%, such as by 200% or more.

The TEG system has been recognized as a uniquely useful tool and has been used extensively in the management of haemostasis during major surgical interventions such as liver transplantations [Kang et al 1985] and cardiovascular procedures as well as obstetrics, trauma, neurosurgery, management of deep vein thrombosis, and the monitoring and differentiation among platelet GPIIb/IIIa antagonists [Di Benedetto 2003]. TEG -guided transfusion therapy aiming at normalising clot strength (MA) has resulted in a reduction in the use of blood products, a reduction in the rate of re-exploration, prediction of bleeding in cardiac surgery. It has also been employed in the monitoring of heart assist devices. The clinical utility of the TEG comes from that this analysis identifies and quantifies the patient's ability to generate thrombin and the resulting physical properties of the clot as well as identifying enhanced fibrinolysis [Rivard et al. 2005].

The data in Example 1 demonstrate that TEG identifies patients at increased risk of organ failure, including MOF, and mortality earlier than conventional coagulation analysis, which are included in different prognostic scores such as the ISTH DIC score. The clinical importance of the TEG result is further illustrated by that patients presenting with a hypocoagulable TEG at ICU admission also had significantly increased APACHE II score and developed higher maximum SOFA score and increased creatinine as compared to patients with a normal TEG upon arrival. Since TEG, but not platelet count differed upon arrival, TEG is able to reflect changes of pathophysiological significance in the haemostatic system earlier and more specifically than routine laboratory parameters. TEG was performed in citrated whole blood and looks beyond the first trace amount of fibrin formed. This technique describes the quality and speed of the entire coagulation and clot formation process. In contrast, commonly used routine laboratory tests are performed in centrifuged plasma fractions and therefore overlook important interactions between the protein coagulation cascade, on the one hand, and platelets and fibrin, on the other hand. The hypocoagulability reflects patients with an increased consumption of platelets that participates in microthrombus formation in vital organs, as illustrated by a higher maximal SOFA score than patients presenting with a normal TEG upon ICU admission.

The hypercoagulability reflects an increased activation of the haemostatic system rendering the platelets hyperreactive, and thus prone to thrombus development.

Identification of Patients at Increased Risk of Development of Organ Failure, Including MOF, by a Viscoelastical Citrated Whole Blood Haemostatic Assay In one embodiment, the invention thus relates to a method of identifying critically ill patients at increased risk of development of organ failure including MOF and TAMOF by analyzing a citrated whole blood sample, such as in a citrated whole blood sample activated by kaolin, such as in a citrated whole blood sample activated by tissue factor, such as in a native whole blood sample, such as a native whole blood sample activated by kaolin, such as in a citrated whole blood sample activated by tissue factor from the patient by a cell based viscoelastical assay upon arrival at the ICU.

In one embodiment, the invention thus relates to a method of identifying critically ill patients at increased risk of development of TAMOF by analyzing a citrated whole blood sample from the patient by the thrombelastography (TEG) system.

In one embodiment, the invention thus relates to a method of identifying critically ill patients at increased risk of development of TAMOF by analyzing a citrated whole blood sample from the patient by the thrombelastometry (ROTEM) systems.

In one embodiment, the invention thus relates to a method of identifying hypocoagulable critically ill patients at risk of development of TAMOF by analyzing a whole blood sample from the patient by the thrombelastography (TEG) and/or thrombelastometry (ROTEM) system.

In one embodiment, the invention thus relates to a method of identifying hypercoagulable critically ill patients at risk of development of TAMOF by analyzing a citrated whole blood sample from the patient by the thrombelastography (TEG) and/or the thrombelastometry (ROTEM) system.

Items

In one embodiment, the invention thus relates to a composition comprising one or more platelet inhibitors and one or more compounds capable of augmenting the fibrinolytic activity.

In one embodiment, the invention thus relates to a composition comprising one or more platelet inhibitors and one or more TAFIa inhibitors.

In one embodiment, the invention thus relates to a composition comprising one or more compounds capable of modulating/preserving the endothelial integrity and one or more compounds capable of augmenting the fibrinolytic activity.

In one embodiment, the invention thus relates to a composition comprising one or more compounds capable of modulating/preserving the endothelial integrity and one or more TAFIa inhibitors.

In one embodiment, the invention thus relates to a composition wherein the platelet inhibitor capable of inhibiting the platelet GPIIb/IIIa receptor is administered together with an inhibitor of thromboxane synthase.

In one embodiment, the invention thus relates to a composition, wherein the platelet inhibitor is capable of inhibiting the platelet COX1 and/or COX2 pathways such as salicylates, arylalkanoic acids, 2-Arylpropionic acids, N-Arylanthranilic acids, pyrazolidine derivatives and oxicams.

In one embodiment, the invention thus relates to a composition wherein the platelet inhibitor is capable of inhibiting Thromboxane-synthase, such as Flavonoids, such as Apigenin, and TP-antagonists such as SQ29548, Bay u 3405, BM 13.177.

In one embodiment, the invention thus relates to a composition wherein the platelet inhibitor is capable of inhibiting adenosine uptake in the platelets such as dipyramidol such as Persantin, Asasantin, Aggrenox.

In one embodiment, the invention thus relates to a composition wherein the platelet inhibitor is capable of inhibiting the platelet GPIb receptor, such as mAB Ib-23, mAB 6B4, R9alpha557 peptide, aurintricarboxylic acid (ATA), crotalin, agkistin, peptide (Trp-Ile-Arg-Arg-Pro-Phe-Phe-Pro-Phe) from alpha B-crystallin In one embodiment, the invention thus relates to a composition wherein the platelet inhibitor is capable of inhibiting the platelet GPVI receptor, such as EXP3179, triplatin-1 and -2, JAQ1, mAB 10B12, mAB 1C3, mAb 12G1.

In one embodiment, the invention thus relates to a composition wherein the platelet inhibitor is capable of inhibiting the platelet PAR receptors, such as thrombin inhibitors, heterocycle-based peptide-miimetic antagonists of PAR-1, RWJ-56110 and RWJ-58259, SCH 79797 SCH 203099 and PAR4 antagonists such as trans-cinnamoyl-YPGKF-amide (tc-Y-NH(2)) and palmitoyl-SGRRYGHALR-amide (P4pal10), PAR-2 antagonist ENMD-1068, PAR2 monoclonal antibody SAM-11.

In one embodiment, the invention thus relates to a composition wherein the platelet inhibitor is Phosphodiesterase inhibitor PDE3 such as Cilostazol.

In one embodiment, the invention thus relates to a composition wherein the platelet inhibitor is Nitroaspirin (NCX4016).

In one embodiment, the invention thus relates to a composition wherein the platelet inhibitor is a Polyethylene Glycol-Conjugated Albumin.

In one embodiment, the invention thus relates to a composition wherein the compound capable of modulating/preserving the endothelial integrity is selected from the group consisting of CD39 and CD73.

In one embodiment, the invention thus relates to a composition wherein the compound capable of modulating/preserving the endothelial integrity is a compound involved in redox control of endothelial functions.

In one embodiment, the invention thus relates to a composition wherein the compound capable of modulating/preserving the endothelial integrity is selected from the group consisting of L-Arginine and tetrahydrobiopterin, Antioxidants (Ascorbate, Glutathione, .alpha.-tocopherol, ubiquinol-10, Probucol), Iron chelators, Polyphenols In one embodiment, the invention thus relates to a composition wherein the compound capable of modulating/preserving the endothelial integrity is selected from the group consisting of HMG-CoA reductase inhibitors (Fluvastatin, Lovastatin, Pravastatin, Simvastatin), Angiotensin-receptor antagonists and ACE inhibitors (Captopril, Zofenopril, Enalapril, Ramipril, Quinapril, Perindopril, Lisinopril, Benazepril, Fosinopril, Casokinins, lactokinins), Peroxisome proliferator-activated receptors (PPARs), NADPH oxidase, Xanthine oxidase, PETN, Heparan sulfates (PI-88), heparan sulfate mimetics, Activators of oxidized/heme-free sGC (BAY 58-2667), Anti-PECAM/SOD.

In one embodiment, the invention thus relates to a composition wherein the compound capable of modulating/preserving the endothelial integrity is Honokiol.

In one embodiment, the invention thus relates to a composition wherein the compound capable of modulating/preserving the endothelial integrity is a compound that directly modulates endothelial barrier function through modulating effects on sphingosine-1-phosphate (S1P)-receptors.

In one embodiment, the invention thus relates to a composition wherein the compound capable of modulating/preserving the endothelial integrity is selected from the group consisting of TY720, AA-R, AAL-S, KRP-203, AUY954, CYM-5442, SEW2871, W146, W140, VPC44116, VPC23019, JTE-013).

In one embodiment, the invention thus relates to a composition wherein the compound capable of modulating/preserving the endothelial integrity is an antibody and/or another molecule against/antagonizing histones through their inhibition histone-mediated endothelial damage and/or microthrombi formation and/or fibrin deposition.

In one embodiment, the invention thus relates to a composition wherein the compound capable of modulating/preserving the endothelial integrity is a compound enhancing the natural anticoagulant pathways and hence protecting the endothelium such as but not exclusively: Protein C pathway (Activated protein C (APC, Drotrecogin alfa), protein C, compounds that either mimics and/or protects from degradation and/or enhances soluble thrombomodulin and/or EPCR and/or protein S), Antithrombin III (ATIII) (or ATIII like compounds and/or compounds that enhance ATIII function) and tissue factor pathway inhibitor (TFPI) (or TFPI compounds and/or compounds that enhance TFPI function).

In one embodiment, the invention thus relates to a composition wherein the compound capable of modulating/preserving the endothelial integrity is a compound that maintain and/or promote Gβγ function and/or signalling following endothelial PAR activation to ensure reannealing of adherens junctions opened following inflammatory PAR mediated activation of Gα.

In one embodiment, the invention thus relates to a composition wherein the compound capable of augmenting the fibrinolytic activity is selected from the group consisting of tissue plasminogen activators such as: Alteplase, Tenecteplase, Reteplase, Streptokinase.

In one embodiment, the invention thus relates to a TAF1a inhibitor for prevention or treatment of organ failure, including multi organ failure, defined as microthrombosis in at least one organ, such as in at least two organs.

In one embodiment of the invention the TAF1a inhibitor is selected from the group consisting of CPU-1, AZD9684, MERGETPA, Compound 21 (UK-396,082).

In one embodiment of the invention the compound capable of inhibiting the platelet GPIIb/IIIa receptor is administered together with an inhibitor of thromboxane synthase.

In one embodiment of the invention the platelet inhibitor is capable of inhibiting the platelet COX1 and/or COX2 pathways such as salicylates, arylalkanoic acids, 2-Arylpropionic acids, N-Arylanthranilic acids, pyrazolidine derivatives and oxicams. 55-60

In one embodiment of the invention the platelet inhibitor is capable of inhibiting Thromboxane-synthase, such as Flavonoids, such as Apigenin, and TP-antagonists such as SQ29548, Bay u 3405, BM 13.177.

In one embodiment of the invention the platelet inhibitor is capable of inhibiting adenosine uptake in the platelets such as dipyramidol such as Persantin, Asasantin, Aggrenox.

In one embodiment of the invention the platelet inhibitor is capable of inhibiting the platelet GPIb receptor, such as mAB Ib-23, mAB 6B4, R9alpha557 peptide, aurintricarboxylic acid (ATA), crotalin, agkistin, peptide (Trp-Ile-Arg-Arg-Pro-Phe-Phe-Pro-Phe) from alpha B-crystallin In one embodiment of the invention the platelet inhibitor is capable of inhibiting the platelet GPVI receptor, such as EXP3179, triplatin-1 and -2, JAQ1, mAB 10B12, mAB 1C3, mAb 12G1.

In one embodiment of the invention the platelet inhibitor is capable of inhibiting the platelet PAR receptors, such as thrombin inhibitors, heterocycle-based peptide-miimetic antagonists of PAR-1, RWJ-56110 and RWJ-58259, SCH 79797 SCH 203099 and PAR4 antagonists such as trans-cinnamoyl-YPGKF-amide (tc-Y-NH(2)) and palmitoyl-SGRRYGHALR-amide (P4pal10), PAR-2 antagonist ENMD-1068, PAR2 monoclonal antibody SAM-11.

In one embodiment, the invention thus relates to a compound capable of augmenting the fibrinolytic activity in whole blood for prevention or treatment of organ failure, wherein organ failure is defined as altered organ function in an acutely ill patient requiring medical intervention to achieve homeostasis; organ failure includes as used herein MOF and TAMOF, in at least one organ, such as in at least two, three, four or five organs.

In one embodiment of the invention the compound capable of augmenting the fibrinolytic activity in whole blood is selected from the group consisting of tissue plasminogen activators such as: Alteplase, Tenecteplase, Reteplase, Streptokinase.

In one embodiment, the invention thus relates to a TAF1a inhibitor for prevention or treatment of organ failure, including multi organ failure, wherein organ failure is defined as altered organ function in an acutely ill patient requiring medical intervention to achieve homeostasis; organ failure includes as used herein MOF and TAMOF, in at least one organ, such as in at least two, three, four or five organs.

In one embodiment of the invention the TAF1a inhibitor is selected from the group consisting of CPU-1, AZD9684, MERGETPA, Compound 21 (UK-396,082).

In one embodiment, the invention thus relates to a compound for the treatment or prophylaxis of TAMOF in patients with malignant diseases such as, but not limited to, solid tumours, haematological malignancies, metastatic tumours, In one embodiment, the invention thus relates to a compound for the treatment or prophylaxis of TAMOF in patients undergoing transplantation. With transplantation means solid organs such as heart, lungs, liver, kidneys, pancreas, intestines or any combination hereof.

In one embodiment, the invention thus relates to a compound for the treatment or prophylaxis of TAMOF in patients undergoing transplantation of allogenic or autologous haematopoietic stem cells, bone marrow, T-cells, B-cells are referred to. Furthermore treatment of a complication of allogenic transplantation, graft versus host disease and/or graft rejection (host vs. graft) is included herein.

In one embodiment, the invention thus relates to a compound for the treatment or prophylaxis of TAMOF in patients secondary to extracorporeal circulation such as but not limited to patients undergoing cardiopulmonary bypass, on ECMO treatment, receiving ventricular assist devices, receiving non-biologic valvular prosthesis.

In one embodiment, the invention thus relates to a compound for the treatment or prophylaxis of TAMOF in patients with vascular prosthesis in any location in the human organism.

In one embodiment, the invention thus relates to a compound for the treatment or prophylaxis of TAMOF in patients with autoimmune diseases such as but not limited to rheumatoid arthritis (juvenile and/or adult form), systemic lupus erythromatosis, sclerodermia, antiphospholipid antibody syndrome.

In one embodiment, the invention thus relates to a compound for the treatment or prophylaxis of TAMOF in patients with colitis ulcerosa or Mb Crhohn's disease.

In one embodiment, the invention thus relates to a compound for the treatment or prophylaxis of TAMOF in patients with necrotisizing fasceitis.

In one embodiment, the invention thus relates to a compound for the treatment or prophylaxis of TAMOF in patients with burn trauma.

In one embodiment, the invention thus relates to a compound for the treatment or prophylaxis of TAMOF in patients exposed to irradiation.

In one embodiment, the invention thus relates to a compound for the treatment or prophylaxis of TAMOF in patients with obstetric complications such as but not limited to preeclampsia, HELLP syndrome.

In one embodiment the organ failure is due to reperfusion injury following ischemia.

In one embodiment, the invention thus relates to a compound for the treatment or prophylaxis of TAMOF in patients with systemic inflammatory response syndrome.

In one embodiment, the invention thus relates to a compound for the treatment or prophylaxis of TAMOF in patients with acute vascular occlusions such as but not limited to mesenteric thrombosis.

In one embodiment, the invention thus relates to a compound for the treatment or prophylaxis of TAMOF in patients with haemolytic-uraemic syndrome.

In one embodiment, the invention thus relates to a compound for the treatment or prophylaxis of TAMOF in patients with systemic infections (any agent) such as but not limited to bacteria, mycoplasma, mycobacteria, ricketsiae, viral, fungal, protozoal infections.

In one embodiment, the invention thus relates to a compound for the treatment or prophylaxis of TAMOF after surgery or trauma.

In one embodiment, the invention thus relates to a compound for the treatment or prophylaxis of TAMOF in patients with vasculitis such as, but not limited to Behcet's Disease, Buerger's Disease, Central Nervous System Vasculitis, Churg-Strauss Syndrome, Cryoglobulinemia, Giant Cell Arteritis, Henoch-Schonlein Purpura, Microscopic Polyangiitis, Polyarteritis Nodosa, Polymyalgia Rheumatica, Rheumatoid Vasculitis, Takayasu's Arteritis, Wegener's Granulomatosis.

In one embodiment, the invention thus relates to a compound for the treatment or prophylaxis of TAMOF in patients with toxins, such as, but not limited to spider, snake, scorpion, jellyfish, wasp, bee, poison dart frog, honeybee, Cyanotoxins, Pit vipers, such as rattlesnakes.

In one embodiment, the invention thus relates to a method for the treatment or prophylaxis of TAMOF in patients treated with chemotherapy such as but not limited to alkylating agents (L01A) exemplified by Cisplatin, carboplatin and oxaloplatin; Anti-metabolites (L01B) masquerade as purine ((azathioprine, mercaptopurine)) or pyrimidine—which become the building blocks of DNA; Plant alkaloids and terpenoids (L01C) as exemplified by Vincristine, Vinblastine, Vinorelbine, Vindesine, Podophyllotoxin. Taxanes (L01CD) Taxol, Docetaxel. Topoisomerase inhibitors (L01CB and L01XX) topotecan., irinotecan, amsacrine, etoposide, etoposide phosphate, teniposide. Antitumour antibiotics (L01D) dactinomycin, doxorubicin, epirubicin, bleomycin. Monoclonal antibodies such as trastuzumab, cetuximab, rituximab, Bevacizumab.

In one embodiment, the invention thus relates to a method for the treatment or prophylaxis of TAMOF in patients treated with irradiation therapy such as but not limited to conventional external beam radiotherapy, Virtual simulation, 3-dimensional conformal radiotherapy, and intensity-modulated radiotherapy, Radioisotope Therapy (RIT).

In one embodiment, the invention thus relates to compound, herein defined as a pharmaceutical composition comprising one or more of a platelet inhibitor, an endothelial modulator, pro-fibrinolytics and TAFIa-inhibitors either administered alone or in combination of two or three or four compounds for prevention and/or treatment of imminent, suspected or manifest organ failure, wherein organ failure is defined as clinical and/or paraclinical suspected organ dysfunction and/or as altered organ function in an acutely ill patient requiring medical invention to achieve homeostasis; organ failure includes as used herein MOF and TAMOF in at least one organ, such as in at least two, three, four, five or six organs.

In one embodiment, the invention thus relates to a compound for the treatment of or prophylaxis of organ failure due to systemic inflammation or due to severe infections or due to sepsis or due to SIRS and/or CARS or due to coagulopathy or due to trauma (Blunt, penetrating trauma, polytrauma, neurotrauma, minor, major) and/or burns/freezing burns or due to malignant diseases such as haematological malignancies, solid tumours and metastatic tumours or due to ischemia/haemorrhage or due to cardiovascular thromboembolic diseases or due to intoxication.

In one embodiment, the invention thus relates to a compound for the treatment of or prophylaxis of organs, which are subject to failure are selected from the group consisting of cardiovascular, respiratory, renal, haematological, neurological, gastrointestinal and hepatic organs and musculoskeletal, such as heart, vessels, microvasculature, lungs, kidney, bone marrow, brain, gut, pancreas, liver, bones, joints and muscles.

In one embodiment, the invention thus relates to a compound for the treatment of or prophylaxis of organ failure due to Infectious diseases caused by any microorganism exemplified by bacteria (intra-, extracellular, myco-), virus, fungi, parasites, prions) including infections caused by any microorganism in the cardiovascular, respiratory, renal, haematological, neurological, gastrointestinal, hepatic and musculoskeletal organs, such as heart, vessels, microvasculature, lungs, kidney, bone marrow, brain, gut, pancreas, liver, bones, joints and muscles Endocarditis, Meningitis, Encephalitis, diarrhea, Hepatitis, Urinary Tract Infections, Intra-Abdominal Infections, Pneumonia, Pharyngitis, Joint Infections, Skin and Soft Tissue infections.

In one embodiment, the invention thus relates to a compound for the treatment of or prophylaxis of organ failure due to ischemia due to stherosclerosis, thrombi, emboli (cholesterol, fat, air, septic, tissue, foreign body, amniotic fluid), trauma, vascular occlusion, vasculitis, aneurysms, severe anemia and/or microthrombi/emboli/occlusion (imminent, suspected, manifest) in one or more organs or severe infections caused by any microorganism including sepsis, severe sepsis, septic shock, organ failure, MOF, DIC, necrotisizing fasciitis.

In one embodiment, the invention thus relates to a compound for the treatment of or prophylaxis of organ failure due to surgery, trauma and/or burns including SIRS, compensatory anti-inflammatory response syndrome, Shock, tissue hypoperfusion, base deficit, lactate acidosis, MOF, DIC, coagulopathy (hypercoagulability, hypocoagulability, hyperfibrinolysis).

In one embodiment, the invention thus relates to a compound for the treatment of or prophylaxis of organ failure due to malignant diseases and chemotherapeutic/immunosuppressive treatment, solid tumours, haematological malignancies, metastatic tumours.

In one embodiment, the invention thus relates to a compound for the treatment of or prophylaxis of organ failure due to chemotherapy (Alkylating agents (L01A) exemplified by Cisplatin, carboplatin and oxaloplatin; Anti-metabolites (L01B) masquerade as purine ((azathioprine, mercaptopurine)) or pyrimidine; Plant alkaloids and terpenoids (L01C) as exemplified by Vincristine, Vinblastine, Vinorelbine, Vindesine, Podophyllotoxin. Taxanes (L01CD) Taxol, Docetaxel. Topoisomerase inhibitors (L01CB and L01XX) topotecan, irinotecan, amsacrine, etoposide, etoposide phosphate, teniposide. Antitumour antibiotics (L01D) dactinomycin, doxorubicin, epirubicin, bleomycin.

In one embodiment, the invention thus relates to a compound for the treatment of or prophylaxis of organ failure due to monoclonal antibodies such as trastuzumab, cetuximab, rituximab, Bevacizumab.

In one embodiment, the invention thus relates to a compound for the treatment of or prophylaxis of organ failure due to irradiation and/or irradiation therapy (Conventional external beam radiotherapy, Virtual simulation, 3-dimensional conformal radiotherapy, and intensity-modulated radiotherapy, Radioisotope Therapy (RIT))

In one embodiment, the invention thus relates to a compound for the treatment of or prophylaxis of organ failure due to transplantation (heart, lungs, liver, kidneys, pancreas, intestines or any combination hereof), allogenic or autologous haematopoietic stem cells, bone marrow, T-cells, B-cells and their complications such as graft versus host disease (acute, chronic), graft rejection (host vs. graft).

In one embodiment, the invention thus relates to a compound for the treatment of or prophylaxis of organ failure due to extracorporeal circulation, plasmapheresis, leukapheresis, dialysis, renal replacement therapy, vascular prosthesis and/or apheresis treatment, cardiopulmonary bypass, ECMO, ventricular assist devices.

In one embodiment, the invention thus relates to a compound for the treatment of or prophylaxis of organ failure due to non-biologic valvular prosthesis, vascular prosthesis (biological, non-biological) in any location in the human organism.

In one embodiment, the invention thus relates to a compound for the treatment of or prophylaxis of organ failure due to intoxication with alcohol, recreational drugs, iatrogenic (chemotherapy, overdose, interaction, adverse event), snake/insect bites (spider, snake, scorpion, jellyfish, wasp, bee, poison dart frog, honeybee), cyanotoxins, Pit vipers, such as rattlesnakes.

In one embodiment, the invention thus relates to a compound for the treatment of or prophylaxis of organ failure due to cardiovascular diseases like but not exclusively Angina, Atherosclerosis, Cardiomyopathy, Congestive heart failure, Coronary artery disease, Carotid artery disease, Endocarditis, Heart attack (coronary thrombosis, myocardial infarction), Hypertension, Hypercholesterolemia/hyperlipidemia, Peripheral artery disease, Stroke, reperfusion injury following ischemia.

In one embodiment, the invention thus relates to a compound for the treatment of or prophylaxis of organ failure due to systemic autoimmune diseases (Rheumatoid arthritis (juvenile and/or adult form), systemic lupus erythromatosis, sclerodermia, antiphospholipid antibody syndrome, polymyositis, mixed connective tissue disease), Sjogrens syndrome, Fibromyalgia), Sarcoidosis.

In one embodiment, the invention thus relates to a compound for the treatment of or prophylaxis of organ failure due to vasculitis (Behcet's Disease, Buerger's Disease, Central Nervous System Vasculitis, Churg-Strauss Syndrome, Cryoglobulinemia, Giant Cell Arteritis, Henoch-Schonlein Purpura, Microscopic Polyangiitis, Polyarteritis Nodosa, Polymyalgia Rheumatica, Rheumatoid Vasculitis, Takayasu's Arteritis, Wegener's Granulomatosis).

In one embodiment, the invention thus relates to a compound for the treatment of or prophylaxis of organ failure due to allergic diseases including Anaphylaxis, asthma, eosinophil esophagitis, food allergy, urticaria, insect sting allergy, rhinitis, sinusitis, immunodeficiency, mastocytosis.

In one embodiment, the invention thus relates to a compound for the treatment of or prophylaxis of organ failure due to respiratory diseases including Asthma, Bronchitis, Emphysema, Chronic obstructive pulmonary disease, Infections (exemplified by influenza, pneumonia and tuberculosis), Malignancies (Lung cancer), Sarcoidosis, Pleurisy.

In one embodiment, the invention thus relates to a compound for the treatment of or prophylaxis of organ failure due to Renal diseases such as Acute/chronic kidney failure, Acute nephritic syndrome, Atheroembolic renal disease, Chronic nephritis, Nephrotic syndrome, End-stage renal disease, Goodpasture syndrome, Interstitial nephritis, Kidney cancer/damage/infection/injury/stones, Lupus nephritis, Glomerulonephritis, Membranous nephropathy, Nephroblastoma, Nephrocalcinosis, Nephrogenic diabetes insipidus, Nephropathy-IgA, Polycystic kidney disease, Reflux nephropathy, Renal papillary necrosis, Renal tubular acidosis.

In one embodiment, the invention thus relates to a compound for the treatment of or prophylaxis of organ failure due to Hepatic diseases such as Alcoholic liver disease, Cholangiocarcinoma, Hepatitis, Hepatic encephalopathy, Hepatic failure, Liver abscess, Malignant/benign liver tumours, Liver cirrhosis, Liver coagulopathy, Glycogen storage diseases, Portal hypertension, Primary biliary cirrhosis, Primary sclerosing cholangitis.

In one embodiment, the invention thus relates to a compound for the treatment of or prophylaxis of organ failure due to Endocrine diseases like Adrenal disorders (Adrenal insufficiency, Addison's disease, Mineralocorticoid deficiency, Conn's syndrome, Cushing's syndrome, Pheochromocytoma, Adrenocortical carcinoma), Glucose homeostasis disorders (Diabetes mellitus, Hypoglycemia, Idiopathic hypoglycemia, Insulinoma), Metabolic bone disease, Pituitary gland disorders (Diabetes insipidus, Hypopituitarism (or Panhypopituitarism), Pituitary tumors, Hyperprolactinemia, Acromegaly, gigantism, Cushing's disease, Parathyroid gland disorders (Primary/Secondary/Tertiary hyperparathyroidism, Hypoparathyroidism, Pseudohypoparathyroidism), Menstrual function or fertility disorders (Polycystic ovary syndrome), Thyroid disorders (Goiter, Hyperthyroidism and Graves-Basedow disease, Hypothyroidism, Thyroiditis, Thyroid cancer, Tumours of the endocrine glands, Multiple endocrine neoplasia, Autoimmune polyendocrine syndromes).

In one embodiment, the invention thus relates to a compound for the treatment of or prophylaxis of organ failure due to gastrointestinal diseases such as Inflammatory bowel diseases (Colitis ulcerosa, Mb Crohn's disease).

In one embodiment, the invention thus relates to a compound for the treatment of or prophylaxis of organ failure due to Gynaecologic/obstetric diseases such as Obstetric complications (Preeclampsia, eclampsia, HELLP syndrome, amniotic fluid embolism, abruptio placentae).

In one embodiment, the invention thus relates to a compound for the treatment of or prophylaxis of organ failure due to Neurological diseases such as Degenerative diseases (Parkinson's disease, Alzheimer's disease), Stroke, Neurotrauma (brain, spinal cord), Seizure disorders (epilepsy), Malignancies (brain/spinal cord tumors), Infections (meningitis, encephalitis).

In one embodiment, the invention thus relates to a compound for the treatment of or prophylaxis of organ failure due to Haematological diseases such as Malignant (Leukaemia, Myelodysplastic syndrome) and/or Non-malignant (Thrombotic thrombocytopenic purpura, haemolytic-uraemic syndrome, aplastic anaemia, Hemophagocytic Lymphohistiocytosis).

In one embodiment, the invention thus relates to a compound for the treatment of or prophylaxis of organ failure due to Orthopedic diseases such as Trauma, Surgery, Fractures, Malignancies of bone, cartilage and soft tissues including Multiple Myeloma, Arthritis (Osteoarthritis, Rheumatoid arthritis), Cerebral Palsy, Osteonecrosis, Gout, Infections, Myasthenia, Osteoporosis, Pagets disease, Spondylitis.

Detailed Description Of Drawings

FIG. 1: Recording haemostatic activity using Thrombelastography (TEG): TEG records the viscoelastic changes during coagulation by analysis of whole blood placed in a rotating cup. A pin is suspended in the blood from a torsion wire, and its resistance to motion is recorded. Four parameters are routinely reported: R (reaction time) denotes the latency from the time at which the blood is placed in the cup until the clot begins to form; the angle (Angle) represents the progressive increase in clot strength; the maximum amplitude (MA) reflects the maximal clot strength; and lysis (Ly30) reflects clot lysis.

Figure 2:
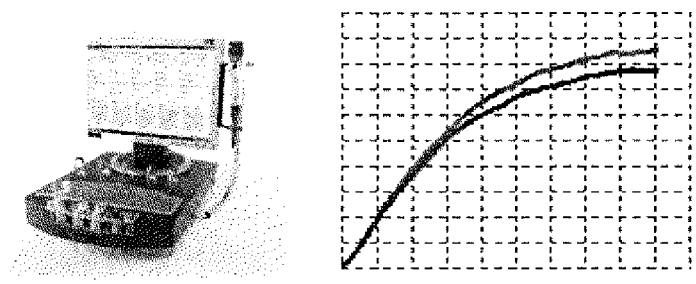
FIG. 2: MultiPlate continuously records platelet aggregation. The increase of impedance by the attachment of platelets onto the Multiplate sensors is transformed to arbitrary aggregation units (AU) and plotted against time.

FIG. 2: Multiplate whole blood aggregometry is a platelet function test, (Multiplate®, Dynabyte Medical, Munich, Germany). This test is based on multiple electrode platelet aggregometry (MEA), which measures platelet aggregation in whole blood (WB) after stimulation with selective platelet agonists such as trombinactivated peptide (TRAP), ADP, ASPI and COLlagen. The increase of impedance by the attachment of platelets onto the Multiplate sensors is transformed to arbitrary aggregation units (AU) and plotted against time. Multiplate thereby allows analyzing the effect of antithrombotic drugs like aspirin, clopidogrel and prostacycline on platelet aggregation.

Figure 3:
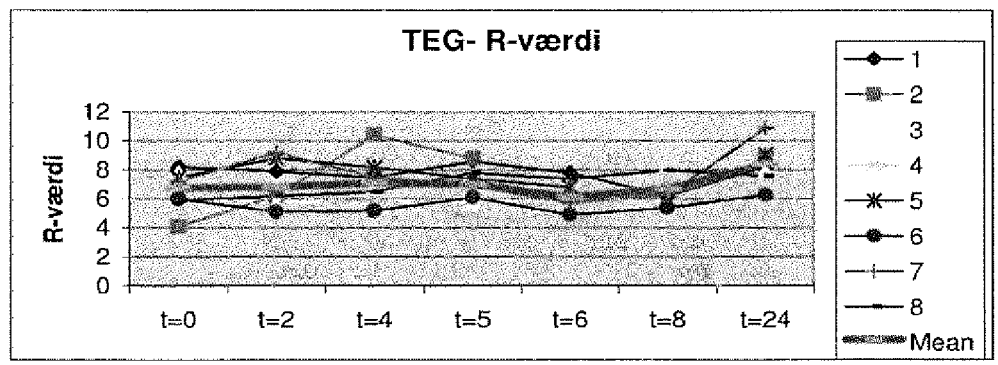
FIG. 3: Comparison of baseline TEG values with samples obtained after 60- and 120 min of flolan infusion.
Figure 3:
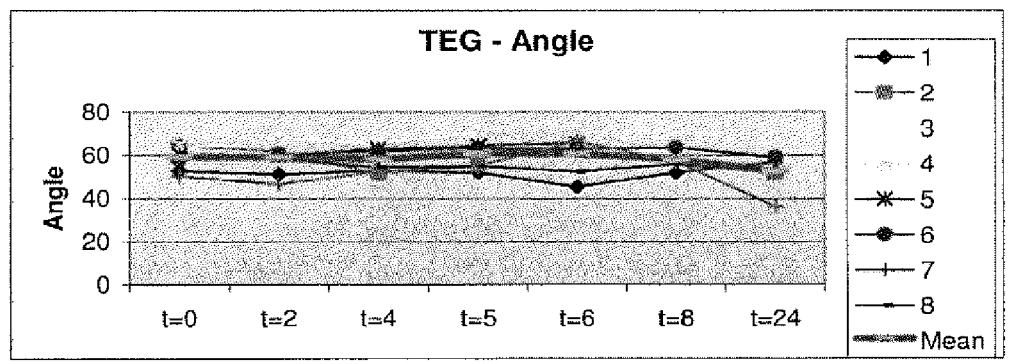
Figure 3:
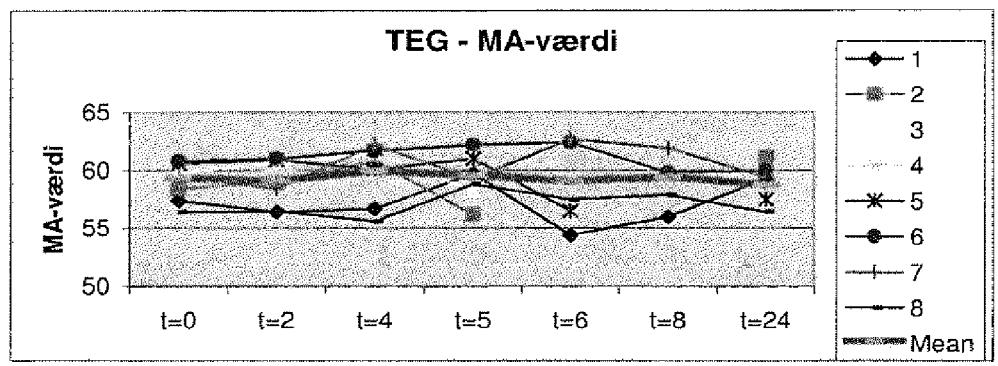

FIG. 3: Comparison of baseline TEG values with samples obtained after 60- and 120 min of flolan infusion.

Figure 4:
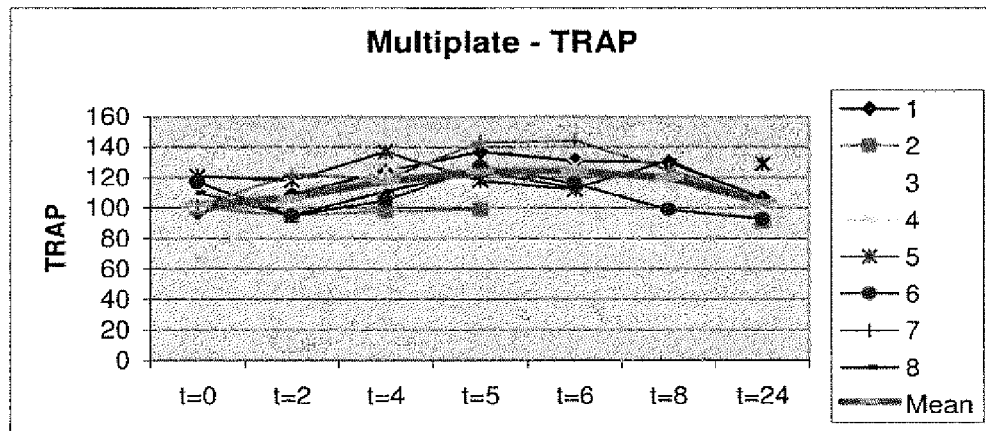
FIG. 4: Comparison of baseline Multiplate values with samples obtained after 60- and 120 min of flolan infusion.
Figure 4:
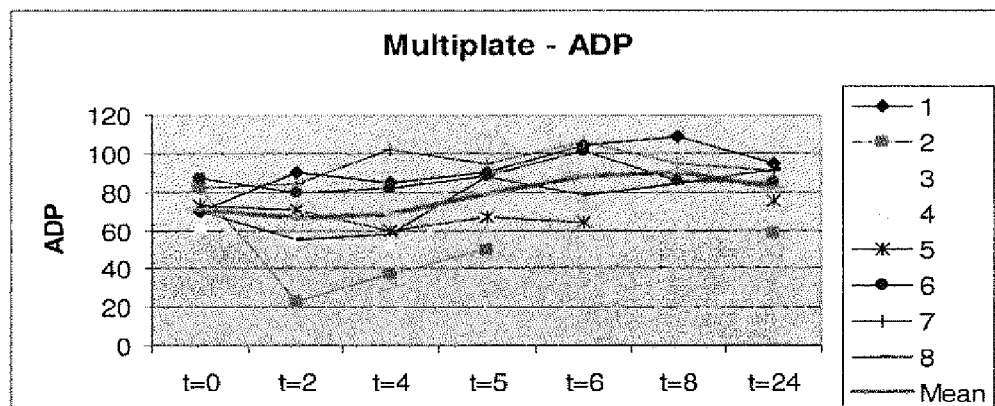

FIG. 4: Comparison of baseline Multiplate values with samples obtained after 60- and 120 min of flolan infusion.

EXAMPLES

Example 1

It has now surprisingly been found that in critically ill patients the TEG result upon arrival to the ICU predicts 30 and 90-day mortality. In 88 medical ICU patients, none of the conventional laboratory analysis including APTT, PT, INR, platelet count, D dimer, CRP or haemoglobin differed at admission between 30-day survivors (n=51) and non-survivors (n=37). The TEG at admission, however, differed significantly between survivors and non-survivors, respectively in all three aspects of the haemostatic process R 6.4 (±2.7) vs. 8.07 (±3.0), p=0.002; Angle 61.0 (±13.1) vs. 51.7 (±18.0), p=0.01; MA 57.3 (±13.0) vs. 49.4 (±17.8),p=0.02.

Thus, a prolonged R was associated with a 3.7 (95% Cl 1.3-10.0) increased odds ratio (unadjusted) for 30-day mortality, a decreased Angle with a 3.8 (95% 1.6-9.5) increased odds ratio (unadjusted) for mortality, and a decreased MA with a 2.8 (95% Cl 1.2-6.8) increased odds ratio (unadjusted) for 30-day mortality. Multivariate logistic regression with use of the significant associated variables (age and APACHE II) was repeated twice for the 88 medical patients identifying R>8 minutes as an independent risk factor for mortality (adjusted OR 3.8; 95% Cl 1.3-11.3) after adjustment for age >65 years (adjusted OR 1.9; 95% Cl 0.7-5) and APACHE II >25 (adjusted OR 4.1; 95% Cl 1.6-10.7). Hosmer and Lemeshow Goodness-of-Fit test, p=0.85.

Also MA<50 mm, was an independent risk factor for mortality (adjusted OR 3.0; 95% Cl 1.1-8.0) after adjustment for age >65 years (adjusted OR 2.5; 95% Cl 0.9-7.2) and APACHE II >25 (adjusted OR 3.5; 95% Cl 1.3-9.0). Hosmer and Lemeshow Goodness-of-Fit test, p=0.68. Consequently a hypocoagulable TEG result upon arrival in these patients may represent a therapeutic target.

Furthermore, patients presenting with hypercoagulability defined as a R<4 min and/or Angle>78° and/or MA>69 mm had a higher survival rate than patients being hypocoagulable (74% vs. 54%) but a lower survival rate than patients presenting with a normal TEG result upon ICU admission (74% vs. 87%), emphasizing that perturbations in coagulability, in either the hypo or hyper direction, have a negative predictive value for clinical outcome in these critically ill patients.

These data demonstrate that TEG identifies patients at increased risk of organ failure, including MOF, and mortality earlier than conventional coagulation analysis, which are included in different prognostic scores such as the ISTH DIC score. The clinical importance of the TEG result is further illustrated by that patients presenting with a hypocoagulable TEG at ICU admission also had significantly increased APACHE II score and developed higher maximum SOFA score and increased creatinine as compared to patients with a normal TEG upon arrival. Since TEG, but not platelet count differed upon arrival, TEG is able to reflect changes of pathophysiological significance in the haemostatic system earlier and more specifically than routine laboratory parameters. TEG was performed in citrated whole blood and looks beyond the first trace amount of fibrin formed. This technique describes the quality and speed of the entire coagulation and clot formation process. In contrast, commonly used routine laboratory tests are performed in centrifuged plasma fractions and therefore overlook important interactions between the protein coagulation cascade, on the one hand, and platelets and fibrin, on the other hand. The hypocoagulability reflects patients with an increased consumption of platelets that participates in microthrombus formation in vital organs, as illustrated by a higher maximal SOFA score than patients presenting with a normal TEG upon ICU admission.

The hypercoagulability reflects an increased activation of the haemostatic system rendering the platelets hyperreactive and thus prone to thrombus development.

Example 2

Ninety-four critically ill patients admitted to the intensive care unit (ICU) underwent haemofiltration with or without concomitant Flolan (prostacyclin) treatment. Flolan was administered in a low dose of 4-6 ng/kg/min in the filters to prevent these from clotting and consequently there was only a minor spill over of Flolan to the systemic circulation. The patients were retrospectively reviewed.

TABLE 6

|  | Flolan group (n = 24) | Non-Flolan group (n = 70) |
|---|---|---|
| APACHE II score (mean) | 26 | 28 |
| Platelet count (difference before vs. after haemofiltration) | +14 | −17 |
| 90 day survival (%) | 67 | 47 |

APACHE II: Acute Physiology and Chronic Health Evaluation II,
ICU: Intensive Care Unit The two groups (Flolan vs. non-flolan) were comparable in regards to APACHE II at admission. However, patients in the flolan group were more severely ill as evaluated by a lower platelet count at start of hemofiltration, a higher frequency of severe thrombocytopenia, a higher frequency of DIC diagnoses, a higher maximum SOFA score and a higher SOFA score at hemofiltration initiation as compared to the patients receiving non-flolan. The finding of increased total transfusion requirements and specifically of FFP during hemofiltration in the flolan group vs. the non-flolan group might thus be attributed to the higher disease severity and associated coagulopathy and not to an increased risk of bleeding due to the use of flolan as anticoagulant. Importantly, when comparing mortality between groups, we found that the flolan group tended to have decreased mortality at 30 days (21% vs. 39%, p=0.12), 90 days (34% vs. 53%, p=0.10) and 365 days (38% vs. 57%, p=0.09).

Flolan does not negatively influence the haemostatic competence as evaluated by transfusion requirements in critically ill patients undergoing haemofiltration and thereby questions the assumption that prostacycline is a powerful antithrombotic agent.

Furthermore, the significant decrease in mortality observed in haemofiltrated patients receiving flolan in the filters indicate that the minor systemic spill-over affects the endothelium, limiting the pro-coagulant effects of systemic inflammation and coagulation activation preventing microvascular occlusion and organ failure.

Example 3

Six healthy volunteers were administered flolan (prostacyclin) intravenously at a dose of 4 ng/kg/min for 2 h. Blood samples for whole blood viscoelastical assay (Thrombelastography [TEG]) and whole blood platelet aggregation (Multiplate) was obtained before infusion of Flolan, after 60 min infusion of Flolan and after 120 min infusion of Flolan.

With regard to the TEG assay this was performed as recommended by the manufacturer and 340 µl are mixed with 20 µl CaCl 0.2 M (final concentration 11.1 mM in the cup) and kaolin at 37° C. after which the haemostatic activity is recorded as depicted in FIG. 1.

Whole blood impedance aggregometry analyzed by the Multiple Platelet function Analyzer (MultiPlate® analyzer). Analysis employing various platelet agonists: ASPItest (activation by arachidonic acid), COLtest (activation by collagen through the collagen receptor), TRAPtest (activation by TRAP-6 stimulates the thrombin receptor on the platelet surface and ADPtest (activation by ADP stimulates platelet activation by the ADP receptors).

MultiPlate continuously records platelet aggregation. The increase of impedance by the attachment of platelets onto the Multiplate sensors is transformed to arbitrary aggregation units (AU) and plotted against time as depicted in FIG. 2.

Results:

No significant difference was observed when comparing baseline TEG values with samples obtained after 60- and 120 min of flolan infusion for any of the parameters investigated (R, Angle, MA) in any of the 6 volunteers studied, see FIG. 3.

Similarly, no significant difference was observed when comparing baseline Multiplate values with samples obtained after 60- and 120 min of flolan infusion for any of the agonists investigated (ASPI, COL, ADP, TRAP) in any of the 6 volunteers studied, see FIG. 4.

Conclusions:

Infusion of Flolan at the doses recommended for clinical use did not negatively affect whole blood haemostatic competence as evaluated by TEG. Furthermore, with regard to whole blood platelet aggregation, employing various platelet agonists is not affected negatively by flolan infusion indicating that such administration not compromise haemostasis.

Example 4

To test the effect of IV infused GPIIb/IIIa inhibitor and PGI2 on bleeding and thrombosis, a rat endotoxemia model was established employing 12 Sprague Dawley rats, males, 250-300 g. The rats were anaesthesized and three IV catheters were placed (1 for endotoxin infusion and 1 for each of the 2 study drugs or saline (Placebo)).

Group 1 (n=6): Endotoxin+Drugs

Endotoxin (LPS (Sigma-Aldrich, Cat. No. 2762) from *e. coli* strain 026:B6IV injection (5 mg/kg bolus)

IV infusion for 8 hours with a combination of two test drugs

GPIIb/IIIa inhibitor=abciximab=RheoPro [1 mg/kg bolus and 0.250 mikrogram/kg/min]

PGI2=flolan[20 ng/kg/min]

Group 2 (n=6): Endotoxin+Placebo

Endotoxin (LPS (Sigma-Aldrich, Cat. No. 2762) from *e. coli* strain 026:B6) IV injection (5 mg/kg bolus)

IV infusion for 8 hours with saline (placebo)

The animals were sacrificed after 8 hours treatment/placebo after receiving a heparin infusion to avoid post-mortem intravascular fibrin deposition.

Analyses before and after treatment/placebo:

Platelet count, hemoglobin, blood pressure, heart rate

Post-mortem histopathology analyses of bleeding and thrombosis:

CNS, heart, lungs, liver, kidneys and intestine

Results

Rats receiving the study drugs demonstrated a diminished decline in platelet count after 8 hours of endotoxin infusion than the placebo group (−39.4% vs. −63.9%), a diminished increase in heart rate (+4.8% vs. +27.6%) and a diminished drop in blood pressure (+0.7% vs. −20.3%). No differences between groups was found with regard to haemoglobin indicating that the rats treated with the study drug did not bleed Post mortem histopathology demonstrated no evidence of increased bleeding in vital organs in the group receiving the study drugs as compared to the placebo group.

Conclusions

Infusion of a combination of RheoPro (=abciximab=a GPIIb/IIIa inhibitor) and Flolan (prostacyclin) to rats with endotoxaemia resulted in improved maintenance of platelet count and reduced clinical deterioration, as evaluated by reduced increase in heart rate and reduced decline in blood pressure, as compared to rats that received placebo. RheoPro is a potent reversible GPIIb/IIIa platelet inhibitor preventing formation of platelet aggregates in the microcirculation. In addition, flolan, a prostacyclin analogue, maintains endothelial integrity and prevents development of a procoagulant phenotype limiting the interaction between platelets and endothelial cells.

Also, infusion of a combination of RheoPro at a dose twice the recommended dose for humans and Flolan, at a dose 10 times the maximal recommended dose in humans will not result in an increased bleeding tendency as evaluated by hemoglobin and histopathological examination of vital organs including CNS, heart, lungs, liver, kidneys and intestine.

TABLE 7

| | | Prostacyclin and GPIIB/IIa inhibitor | Saline |
|---|---|---|---|
| n | | 6 | 6 |
| Bodyweight | g | 295 | 301 |
| HGB | % change 0-7 hours | −23.6% | −23.1% |
| PLT | % change 0-7 hours | −39% | −70% |
| HR | % change 0-7 hours | 4.8% | 27.6% |
| BP | % change 0-7 hours | 0.7% | −20.3% |

References

Abraham et al., JAMA. 2003 Jul. 9; 290(2):238-47.
Afshari et al., Cochrane Database Syst Rev. 2008 Jul. 16; (3):CD005370.
Atkinson et al., Blood Cells, Molecules, and Diseases 36 (2006) 217-222
Bassus et al., Platelets. 2006 September; 17(6):378-84.
Bernard et al., Crit Care Med. 2001 November; 29(11):2051-9.
Bick R., Semin Thromb Hemost. 1996; 22(1):69-88.
Bick R., Semin Thromb Hemost. 1998; 24(1):3-18.
Bihari et al., Intensive Care Med. 1988; 15(1):2-7

Cines et al., 1998, Blood 91:3527-3561.
Colgan et al., Purinergic Signalling (2006) 2: 351-360.
De Meyer et al., Cardiovasc Hematol Disord Drug Targets. 2009 March; 9(1):9-20
Di Benedetto et al., Minerva Anestesiol. 2003 June; 69(6): 501-9, 509-15.
Fries et al., Anesth Analg. 2006 February; 102(2):347-51.
Ganter et al., Anesth Analg. 2008 May; 106(5):1366-75.
Geerts et al., Chest. 2008 June; 133(6 Suppl):381S-453S.
Goepfert et al., 2000, Molecular Medicine 6(7): 591-603.
Goerge et al. 2008, Blood. 2008 May 15; 111(10):4958-64.
Kanaan et al., Clin Ther. 2007 November; 29(11):2395-405.
Kang et al., Anesth Analg. 1985 September; 64(9):888-96.
Kawasaki et al., Stroke. 2000 March; 31(3):591-5.
Knezevic et al., Exp Med. 2009 Nov. 23; 206(12):2761-77
Levi M., Curr Opin Hematol. 2008 September; 15(5):481-6.
Levi and Lowenberg, Semin Thromb Hemost 2008; 34(5): 417-424.
Marsolais et al., Nat Rev Drug Discov. 2009 April; 8(4):297-307.
Marti-Carvajal et al., Cochrane Database Syst Rev. 2007 Jul. 18; (3):CD004388.
Review. Update in: Cochrane Database Syst Rev. 2008; (1): CD004388.
Moreau et al., Chest 2007; 131(6):1735-1741.
Nachman and Rafii, N Engl J Med, 2008; 359:1261-70.
Nguyen and Carcillo, 2006, Critical Care 2006, 10:235.
de Oliveira et al., J Thromb Thrombolysis. 2009 Aug. 25
Rivard et al., 2005, Journal of Thrombosis and Haemostasis, 4: 411-416
Roberts et al. 2006 Semin Thromb Hemost. 2006 April; 32 Suppl 1:32-8
Salooja et al., Blood Coagul Fibrinolysis. 2001 July; 12(5): 327-37. Review. Erratum in: Blood
Coagul Fibrinolysis 2002 January; 13(1):75.
Schereen et al., Intensive Care Med (1997) 23: 146-158
Thompson et al., J. Exp. Med. Volume 200, Number 11, Dec. 6, 2004 1395-1405
Tomokiyo et al., Vox Sang. 2003 November; 85(4):290-9.
Velik-Salchner et al., J Thromb Haemost. 2007 May; 5(5): 1019-25.
Xu et al., Nat Med. 2009 November; 15(11):1318-21.
Zardi et al., International Immunopharmacology 5 (2005) 437-459
Zardi et al., Prostaglandins & other Lipid Mediators 83 (2007) 1-24
Irish Critical Care Trials Group 2008
American College of Chest Physicians/Society of Critical Care Medicine Consensus Conference (Bone et al. 1992)

The invention claimed is:

1. A method of treating or reducing risk of systemic inflammation and/or severe infection, in a patient suffering from systemic inflammation and/or severe infection characterized by purpura fulminans; comprising administering to a patient in need thereof a combination of (1) one or more compounds selected from the group consisting of platelet inhibitors, wherein the platelet inhibitor is capable of inhibiting the GPIIb/IIIa receptor and (2) one or more compounds capable of modulating/preserving the endothelial integrity wherein the compound capable of modulating/preserving the endothelial integrity is selected from the group consisting of PGI2, PGX, and prostacyclin or a variant thereof, thereby treating or preventing organ failure in said patient.

2. The method of claim 1, wherein the platelet inhibitor is capable of inhibiting the GPIIb/IIIa receptor and the compound capable of modulating/preserving the endothelial integrity is PGI2 or a variant thereof.

3. The method of claim 1, wherein the platelet inhibitor is selected from the group consisting of abciximab, eptifibatide, tirofiban, orbofiban, xemilofiban, lamifiban, XJ757, DUP728 and XR299.

4. The method of claim 1, wherein the platelet inhibitor has a half time of less than 3 hours.

5. The method of claim 1, wherein the prostacyclin variant is selected from the group consisting of beraprost sodium, epoprostenol sodium, iloprost, iloprost in combination with bosentan, iloprost in combination with sildenafil citrate, treprostinil, pegylated treprostinil, treprostinil diethanolamine and treprostinil sodium, 2-{4-[(5,6-diphenylpyrazin-2-yl)(isopropyl)amino]butoxy}-N-(methylsulfonyl)acetamide, {4-[(5,6-diphenylpyrazin-2-yl)(isopropyl)amino]butoxy-lacetic acid, 8-[1,4,5-triphenyl-1H-imidazol-2-yl-oxy]octanoic acid, isocarbacyclin, cicaprost, [4-[2-(1,1-Diphenyl-ethylsulfanyl)-ethyl]-3,4-dihydro-2H-benzo[1,4] oxazin-8-yloxy]-acetic acid N-Methyl-d-glucamine, 7,8-dihydro-5-(2-(1-phenyl-1-pyrid-3-yl-methiminoxy)-ethyl)-a-naphthyloxyacetic acid, (5-(2-diphenylmethyl aminocarboxy)-ethyl)-a-naphthyloxyaceticacid, 2-[3-[2-(4,5-diphenyl-2-oxazoly)ethyl]phenoxy]acetic acid, [3-[4-(4,5-diphenyl-2-oxazolyl)-5-oxazolyl]phenoxy]acetic acid, bosentan, 17[alpha], 20-dimethyl-[DELTA]6,6a-6a-carba PGI1, 15-deoxy-16[alpha]-hydroxy-16[beta],20-dimethyl-[DELTA]6,6a-6a-carba PGI1 and pentoxifylline (1- {5-oxo-hexyl}-3,7-dimethylxanthine).

6. The method of claim 1, wherein the compound capable of modulating/preserving the endothelial integrity has a half-life of less than 4 hours.

7. A method for the preservation of platelet number and/or function in a patient suffering from systemic inflammation and/or severe infection characterized by purpura fulminans comprising administering to a patient in need thereof a combination of (1) one or more compounds selected from the group consisting of platelet inhibitors, wherein the platelet inhibitor is capable of inhibiting the GPIIb/IIIa receptor, and (2) one or more compounds capable of modulating/preserving the endothelial integrity wherein the compound capable of modulating/preserving the endothelial integrity is selected from the group consisting of PGI2, PGX, nitrogen oxide, and prostacyclin or a variant thereof, thereby treating or reducing risk of purpura fulminans in said patient.

8. The method of claim 7, wherein the platelet inhibitor is capable of inhibiting the GPIIb/IIIa receptor and the compound capable of modulating/preserving the endothelial integrity is PGI2 or a variant thereof.

9. The method of claim 7, wherein the platelet inhibitor is selected from the group consisting of abciximab, eptifibatide, tirofiban, orbofiban, xemilofiban, lamifiban, XJ757, DUP728 and XR299.

10. The method of claim 7, wherein the platelet inhibitor has a half time of less than 3 hours.

11. The method of claim 7, wherein the prostacyclin variant is selected from the group consisting of beraprost sodium, epoprostenol sodium, iloprost, iloprost in combination with bosentan, iloprost in combination with sildenafil citrate, treprostinil, pegylated treprostinil, treprostinil diethanolamine and treprostinil sodium, 2-{4-[(5,6-diphenylpyrazin-2-yl)(isopropyl)amino]butoxyl}-N-(methylsulfonyl)acetamide, {4-[(5,6-diphenylpyrazin-2-yl)(isopropyl)amino]butoxyl acetic acid, 8-[1,4,5-triphenyl-1H-imidazol-2-yl-oxy]octanoic acid, isocarbacyclin, cicaprost, [4-[2-(1,1-Diphenyl-ethylsulfanyl)-ethyl]-3,4-dihydro-2H-benzo[1,4]oxazin-8-yloxy]-acetic acid N-Methyl-d-glucamine, 7,8-dihydro-5-(2-(1-phenyl-1-pyrid-3-yl-methiminoxy)-ethyp-a-naphthyloxyacetic acid, (5-(2-diphenylmethyl aminocarboxy)-ethyl)-a-naphthyloxyaceticacid, 2-[3[-(4,5-diphenyl-2-oxazolypethyl]phenoxy]acetic acid, [3-[4-(4,5-diphenyl-2-oxazolyl)-5-oxazolyl]phenoxy]acetic acid, bosentan, 17[alpha], 20-dimethyl-[DELTA]6,6a-6a-carba PGI1, 15- deoxy-16[alpha]-hydroxy-16[beta],20-dimethyl-[DELTA]6,6a-6a-carba PGI1 and pentoxifylline (1-{5-oxo-hexyl}-3,7-dimethylxanthine).

12. The method of claim 7, wherein the compound capable of modulating/preserving the endothelial integrity has a half-life of less than 4 hours.

13. A method of treating or reducing risk of purpura fulminans, in a patient suffering from systemic inflammation and/or severe infection; comprising administering to a patient in need thereof a combination of (1) one or more compounds selected from the group consisting of platelet inhibitors, wherein the platelet inhibitor is capable of inhibiting the GPIIb/IIIa receptor and (2) one or more compounds capable of modulating/preserving the endothelial integrity wherein the compound capable of modulating/preserving the endothelial integrity is selected from the group consisting of PGI2, PGX, and prostacyclin or a variant thereof, thereby treating or preventing organ failure in said patient.

\* \* \* \* \*